US 9,877,637 B2

(12) United States Patent
Nakajima

(10) Patent No.: US 9,877,637 B2
(45) Date of Patent: Jan. 30, 2018

(54) ENDOSCOPE

(71) Applicant: OLYMPUS CORPORATION, Tokyo (JP)

(72) Inventor: Sho Nakajima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/198,129

(22) Filed: Jun. 30, 2016

(65) Prior Publication Data

US 2016/0302649 A1 Oct. 20, 2016

Related U.S. Application Data

(63) Continuation of application No. PCT/JP2015/057860, filed on Mar. 17, 2015.

(30) Foreign Application Priority Data

Jun. 19, 2014 (JP) ................ 2014-126598

(51) Int. Cl.
| | |
|---|---|
| *A61B 1/00* | (2006.01) |
| *A61B 1/005* | (2006.01) |
| *A61B 1/06* | (2006.01) |
| *G02B 23/24* | (2006.01) |
| *A61B 1/12* | (2006.01) |
| *A61B 1/015* | (2006.01) |

(52) U.S. Cl.
CPC ........ *A61B 1/00142* (2013.01); *A61B 1/0051* (2013.01); *A61B 1/00121* (2013.01); *A61B 1/00128* (2013.01); *A61B 1/00137* (2013.01); *A61B 1/0676* (2013.01); *A61B 1/121* (2013.01); *G02B 23/2476* (2013.01); *A61B 1/015* (2013.01)

(58) Field of Classification Search
CPC .. A61B 1/00068; A61B 1/015; A61B 1/00137
USPC .................................................. 600/132, 159
See application file for complete search history.

(56) References Cited

FOREIGN PATENT DOCUMENTS

| JP | H08086966 A | 4/1996 |
|---|---|---|
| JP | 2004089232 A | 3/2004 |
| JP | 3947270 B1 | 7/2007 |

(Continued)

OTHER PUBLICATIONS

International Search Report dated Jun. 9, 2015 issued in PCT/JP2015/057860.

*Primary Examiner* — Matthew J Kasztejna
(74) *Attorney, Agent, or Firm* — Scully, Scott, Murphy & Presser, P.C.

(57) ABSTRACT

An endoscope includes a partition wall to shield an inner side space and an outer side space, a cylindrical body including an internal wall surface coupled to the partition wall to be capable of being water tight, and forming a communication hole communicating with the inner side space, and including a through-hole piercing through the internal wall surface to an outer circumference, a valve body fixed to the communication hole keeping watertightness and including a check valve section opening and closing according to a pressure difference between the inner side space and the outer side space, a first frame body provided on an outer circumference side of the cylindrical body and is capable of operating in an axial direction of the cylindrical body, a second frame body sheathed over the cylindrical body and the first frame body keeping watertightness, and forming a first space communicating with the through-hole.

11 Claims, 27 Drawing Sheets

(56) References Cited

FOREIGN PATENT DOCUMENTS

| | | |
|---|---|---|
| JP | 2009089765 A | 4/2009 |
| JP | 2013046701 A | 3/2013 |

ENDOSCOPE

CROSS REFERENCE TO RELATED APPLICATION

This application is a continuation application of PCT/JP2015/057860 filed on Mar. 17, 2015 and claims benefit of Japanese Application No. 2014-126598 filed in Japan on Jun. 19, 2014, the entire contents of which are incorporated herein by this reference.

BACKGROUND OF THE INVENTION

1. Field of the Invention

The present invention relates to an endoscope including a communication mechanism that eliminates a difference between an air pressure in an endoscope inside space and an atmospheric pressure in an external space.

2. Description of the Related Art

Before and after use of a conventional endoscope, in particular, a surgical endoscope among medical endoscopes, simple cleaning is performed on the endoscope. Additionally, autoclave sterilization treatment for exposing the endoscope to high-temperature and high-pressure sterilization steam and various kinds of gas sterilization treatments are applied to the endoscope. As the conventional endoscope subjected to such sterilization/disinfecting treatment and the like, there is an endoscope including a pipe sleeve, which includes a check valve that irreversibly performs ventilation from an internal space to an external space, and a ventilation valve adjacent to the pipe sleeve.

In the conventional endoscope having such a form, when the autoclave sterilization treatment or the like is performed, an endoscope internal space changes to a negative pressure state. The negative pressure state means a state in which pressure in the internal space is smaller than an atmospheric pressure in the external space. In this way, in a state in which the internal space remains in the negative pressure state and a difference between the pressure in the internal space and the atmospheric pressure in the external space remains occurred, for example, flexible bending rubber, which covers a bending section of an insertion section is in a press-contact state with a plurality of bending pieces made of metal. When the bending section is bent in that state, it is likely that the bending rubber is damaged because the bending rubber is, for example, rolled in or bit by the bending pieces. An operation switch of an endoscope operation section is sometimes covered by a switch cover made of an elastic body such as rubber. In the case of such a configuration, it is likely that operability of the operation switch and the like is hindered if the internal space remains in the negative pressure. Therefore, in the conventional endoscope of this type, a ventilation valve or the like is provided as a component for, after the sterilization treatment or the like is applied, before use of the endoscope, returning the negative pressure in the internal space to pressure substantially the same as the atmospheric pressure in the external space.

In this case, as a configuration for releasing the negative pressure in the endoscope internal space after the sterilization treatment in order to prevent damage or the like of the endoscope, various ideas have been proposed or put to practical use by, for example, Japanese Patent Application Laid-Open Publication No. 2013-46701, Japanese Patent Application Laid-Open Publication No. 2009-89765, Japanese Patent No. 3947270, and the like.

Means disclosed by Japanese Patent Application Laid-Open Publication No. 2013-46701 is a configuration for, in a process for detaching a sterilization cap from a sterilization pipe sleeve including a check valve mechanism, the sterilization cap pushes in a ventilation valve provided in a vicinity of the sterilization pipe sleeve to thereby bring the endoscope internal space into an open state.

Means disclosed by Japanese Patent Application Laid-Open Publication No. 2009-89765 and Japanese Patent No. 3947270 is a configuration for rotating a sterilization cap to thereby forcibly push in a check valve body of a check valve mechanism resisting an urging spring of the check valve body to bring a check valve into an open state.

On the other hand, means disclosed by Japanese Patent Application Laid-Open Publication No. 2004-89232 is a mechanism that is, in a water leak test, mounted with a connector of a water leak tester to open, without causing a check valve body in a check valve mechanism to operate, a bypass path provided in a portion other than the check valve mechanism.

SUMMARY OF THE INVENTION

An endoscope according to an aspect of the present invention includes: a partition wall configured to shield an inner side space and an outer side space; a cylindrical body including an internal wall surface coupled to the partition wall to be capable of being water tight, the internal wall surface forming a communication hole communicating with the inner side space, and including a through-hole piercing through the internal wall surface to an outer circumference; a valve body fixed to the communication hole while keeping water tightness and including a check valve section that performs opening and closing operations according to a pressure difference between the inner side space and the outer side space; a first frame body provided on an outer circumference side of the cylindrical body and configured to be capable of operating in an axial direction of the cylindrical body; a second frame body sheathed over the cylindrical body and the first frame body while keeping the water tightness, the second frame body forming a first space communicating with the through-hole; and a water-tight member disposed between the cylindrical body and the first frame body, the water-tight member switching opening/closing states of the first space and the outer side space when the first frame body operates in the axial direction.

DETAILED DESCRIPTION OF THE PREFERRED EMBODIMENTS

Figure 1:
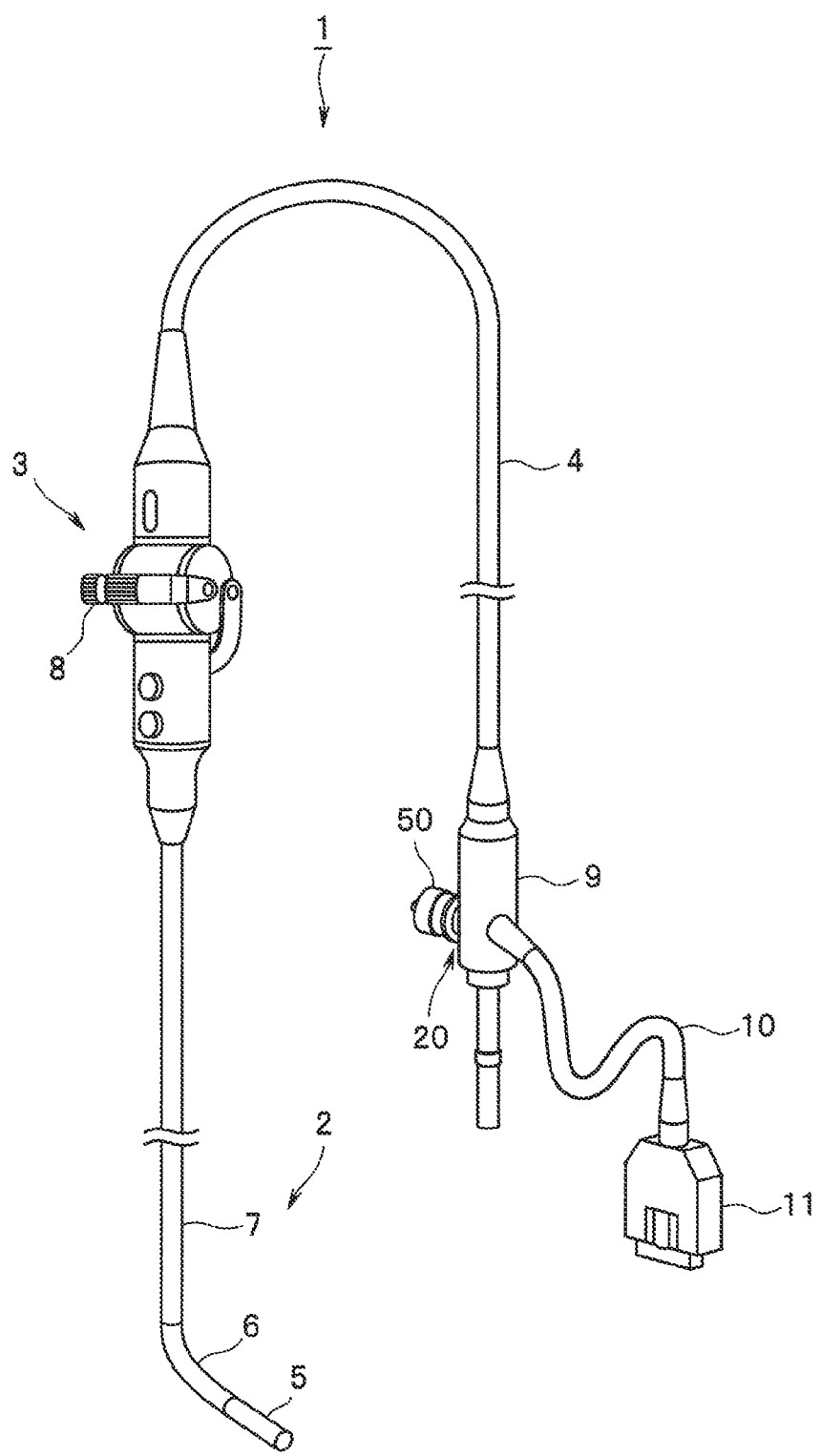
FIG. 1 is a perspective view showing an overall configuration of an endoscope in a first embodiment of the present invention.

The present invention is explained below with reference to embodiments shown in the figures. In the respective drawings used in the following explanation, scales are sometimes varied for each of components to show the respective components in recognizable sizes on the drawings. Therefore, the numbers of the components, shapes of the components, ratios of the sizes of the components, and relative positional relations of the respective components described in the drawings are not limited only to forms shown in the figures.

First Embodiment

First, a schematic configuration of an entire endoscope in a first embodiment of the present invention is explained. FIG. 1 is a perspective view showing an overall configuration of the endoscope in the first embodiment of the present invention.

As shown in FIG. 1, an endoscope 1 in the present embodiment is configured by, for example, an insertion section 2 inserted into a subject such as a body cavity, an operation section 3 consecutively connected to a proximal end side of the insertion section 2 and also functioning as a grasping section, a universal cord 4 extended from the operation section 3 to, for example, a rear side of the operation section 3 and having flexibility.

The insertion section 2 includes, in order from a distal end side, a distal end portion 5 including an objective optical system and an illumination optical system (not shown in the figure), a bending section 6 formed to be bendable, and a flexible tube section 7 having flexibility.

The operation section 3 includes, on an inside, besides various structures, for example, electric components such as an electric circuit board and an electric cable, a bending mechanism and the like for bending the bending section 6 of the insertion section 2 and various conduits, cables, and the like inserted through to the distal end portion 5 of the insertion section 2 via the universal cord 4. On an outer surface of the operation section 3, various operation members such as a bending lever 8 for remotely bending the bending section 6 are disposed.

The universal cord 4 is a tubular member through which, for example, a light guide fiber for transmitting illumination line from a not-shown light-source illumination apparatus and a signal cable connected to a not-shown control unit to transmit various signals are inserted. A light guide connector 9 connectable to a light source apparatus (not shown in the figure), which is an external apparatus, is connected to a terminal end portion of the universal cord 4. Therefore, a light-guide connection terminal is provided at one end of the light guide connector 9. As explained above, the universal cord 4 is consecutively connected to the other end of the light guide connector 9.

Further, a video cable 10 branches and extends from a side of the light guide connector 9. A video connector 11 is connected to a terminal end portion of the video cable 10. The video connector 11 is connected to a camera control unit (not shown). The camera control unit including a video processor function or the like is a control device and a signal processing device. That is, the video connector 11 is a connecting member connecting the endoscope 1 in the present embodiment and the unshown camera control unit (CCU) to perform electric connection therebetween.

On the other hand, a check valve unit 20 for causing an inner side space (hereinafter referred to as internal space) and an outer side space (hereinafter referred to as external space) of the endoscope 1 to communicate with each other and eliminating an inner/outer air pressure difference is inserted through and arranged on one side portion of the light guide connector 9. In the check valve unit 20, a sterilization cap 50 attached at predetermined time, that is, when sterilization treatment or the like (e.g., autoclave sterilization treatment) is applied is detachably disposed as appropriate. The sterilization cap 50 also functions as a lid member for releasing an air pressure in the internal space of the endoscope 1 when being detached after an end of the sterilization treatment.

Note that, in the present embodiment, a configuration in which only the check valve unit 20 is provided as a mechanism for causing an inside and an outside of the endoscope to communicate with each other is illustrated. As a configuration different from this, a ventilation valve unit may be juxtaposed in a vicinity of the check valve unit 20 to configure the endoscope.

In the endoscope 1 in the present embodiment configured as explained above, detailed configurations of the check valve unit 20 and the sterilization cap 50 are explained below with reference to FIG. 2 to FIG. 13.

Figure 2:
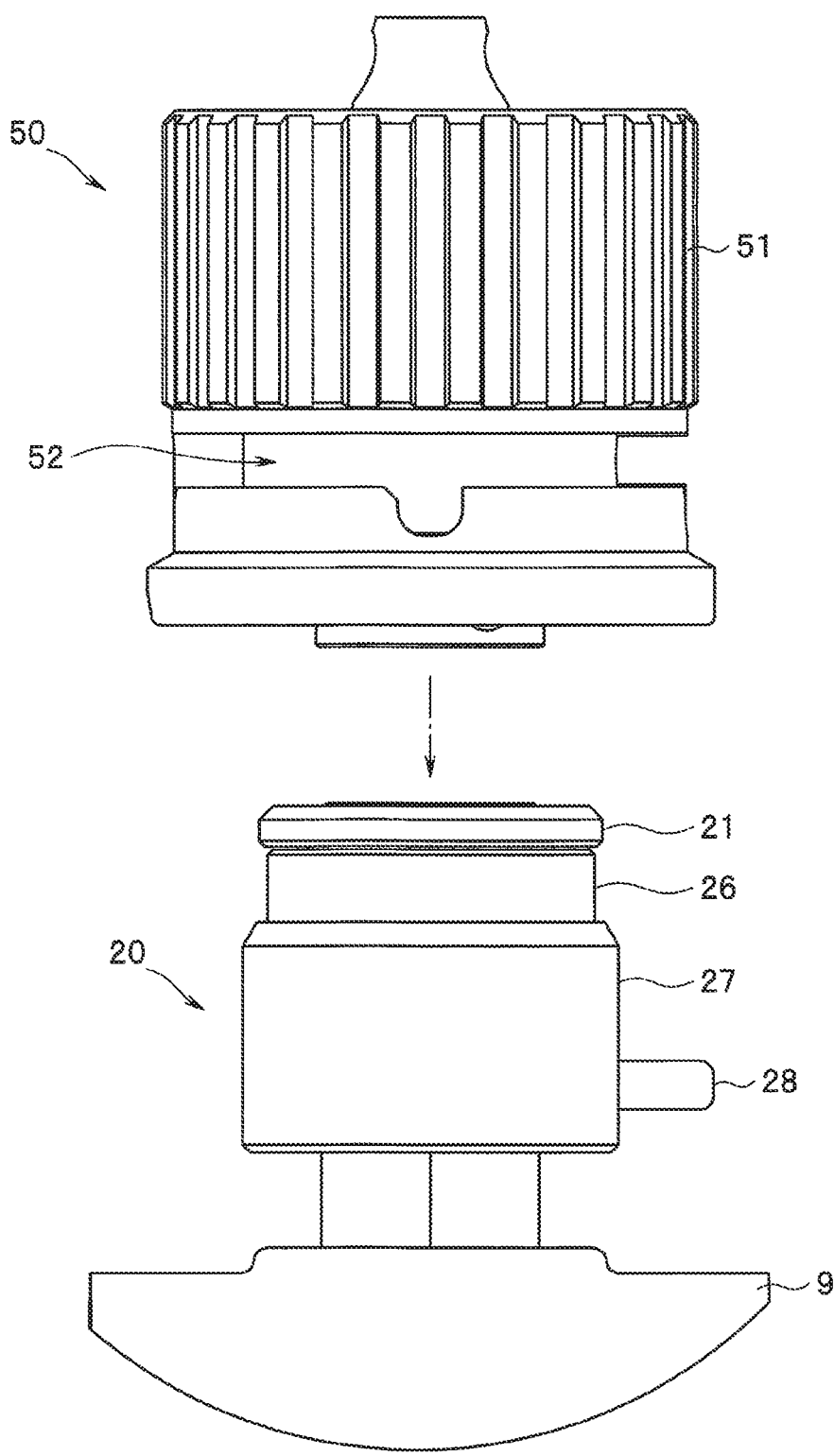
FIG. 2 is an exterior view showing an overview of a check valve unit and a sterilization cap in the endoscope in the first embodiment of the present invention and showing a state in which the sterilization cap is detached from the check valve unit.
Figure 3:
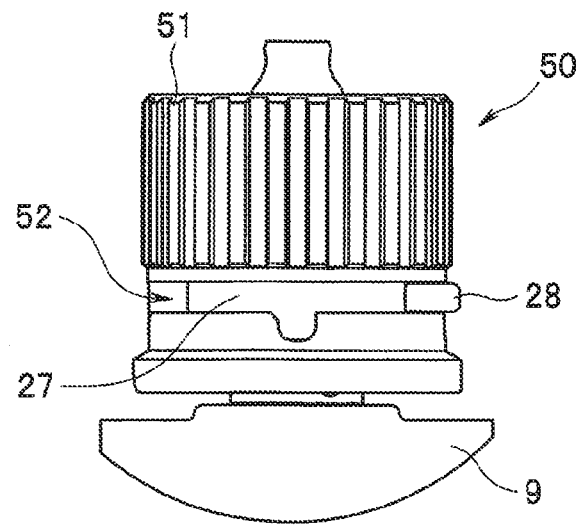
FIG. 3 is a side view in which a state at the time when the sterilization cap is attached to the check valve unit in the state shown in FIG. 2 is viewed from a direction orthogonal to a light guide connector long axis.
Figure 4:
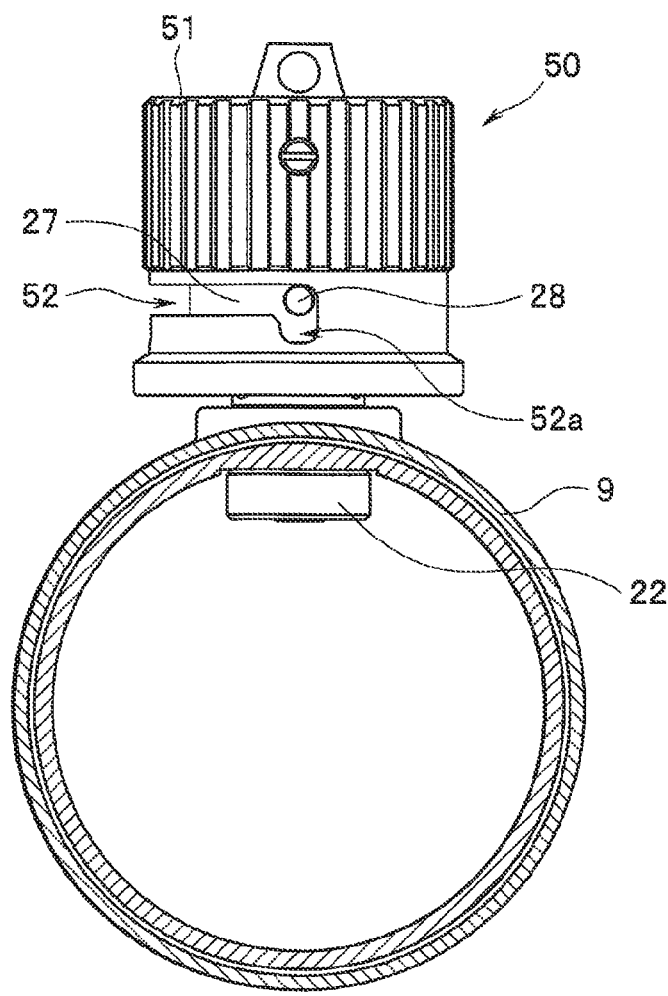
FIG. 4 is a side view in which the state at the time when the sterilization cap is attached to the check valve unit in the state shown in FIG. 2 is viewed from a direction along the light guide connector long axis.

FIG. 2 to FIG. 4 are exterior views showing overviews of the check valve unit and the sterilization cap in the endoscope in the present embodiment. Among the figures, FIG. 2 shows a state in which the sterilization cap is detached from the check valve unit. FIG. 3 and FIG. 4 show a state in which the sterilization cap is attached to the check valve unit. Note that FIG. 2 and FIG. 3 are side views viewed from a direction orthogonal to a long axis of the light guide connector. FIG. 4 is a side view viewed from a direction along the long axis of the light guide connector.

Figure 5:
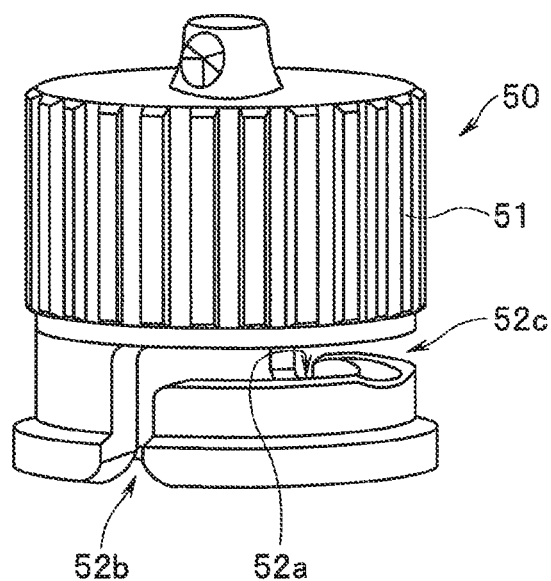
FIG. 5 is an exterior perspective view extracting and showing only the sterilization cap in the endoscope in the first embodiment of the present invention.
Figure 6:
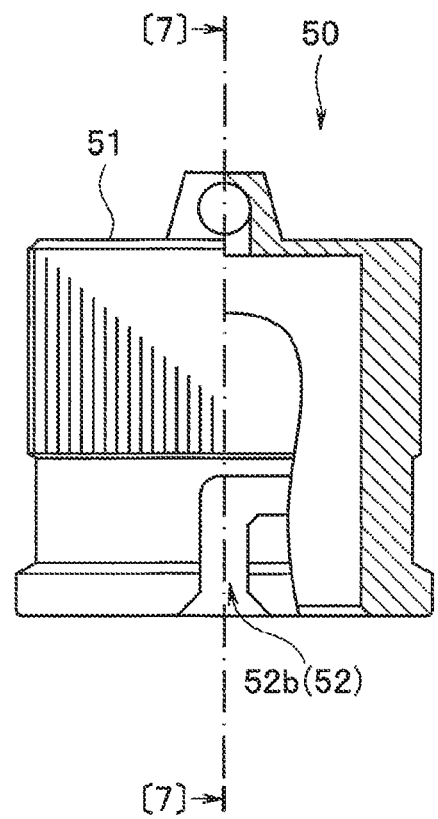
FIG. 6 is a partial sectional view showing, as a cross section, a part of the sterilization cap shown in FIG. 5.
Figure 7:
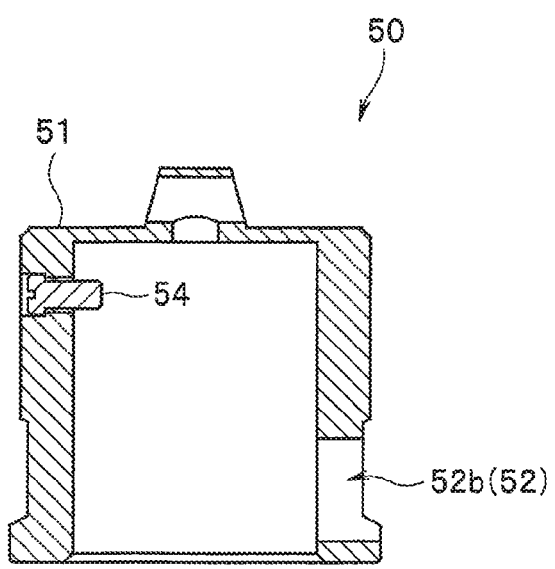
FIG. 7 is a sectional view taken along line [7]-[7] in FIG. 6.

FIG. 5 to FIG. 7 are figures extracting and showing only the sterilization cap. Of the figures, FIG. 5 is an exterior perspective view showing an exterior of the sterilization cap. FIG. 6 is a partial sectional view showing, as a cross section, a part of the sterilization cap. FIG. 7 is a sectional view showing another cross section (different from FIG. 6) of the sterilization cap. Note that FIG. 6 shows a side cross section viewed from a lead-in section 52*b* side of a guide groove 52.

FIG. 7 shows a cross section taken along a surface on which the guide groove 52 is cut, that is, a cross section taken along line [7]-[7] in FIG. 6.

Figure 8:
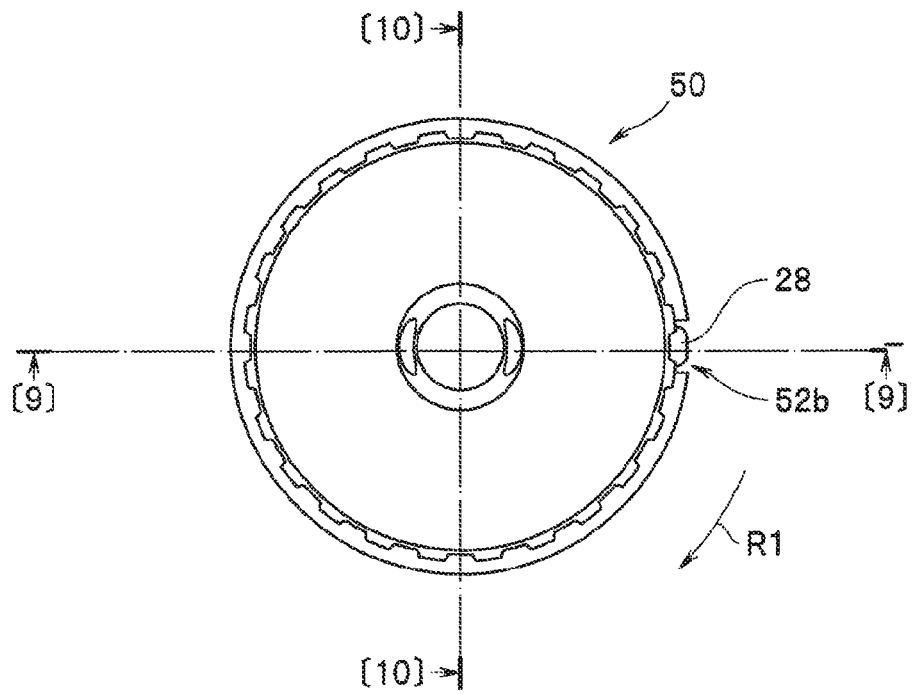
FIG. 8 is a top view during a closed state of a communication path in a state in which the sterilization cap is attached to the check valve unit in the endoscope in the first embodiment of the present invention.
Figure 9:
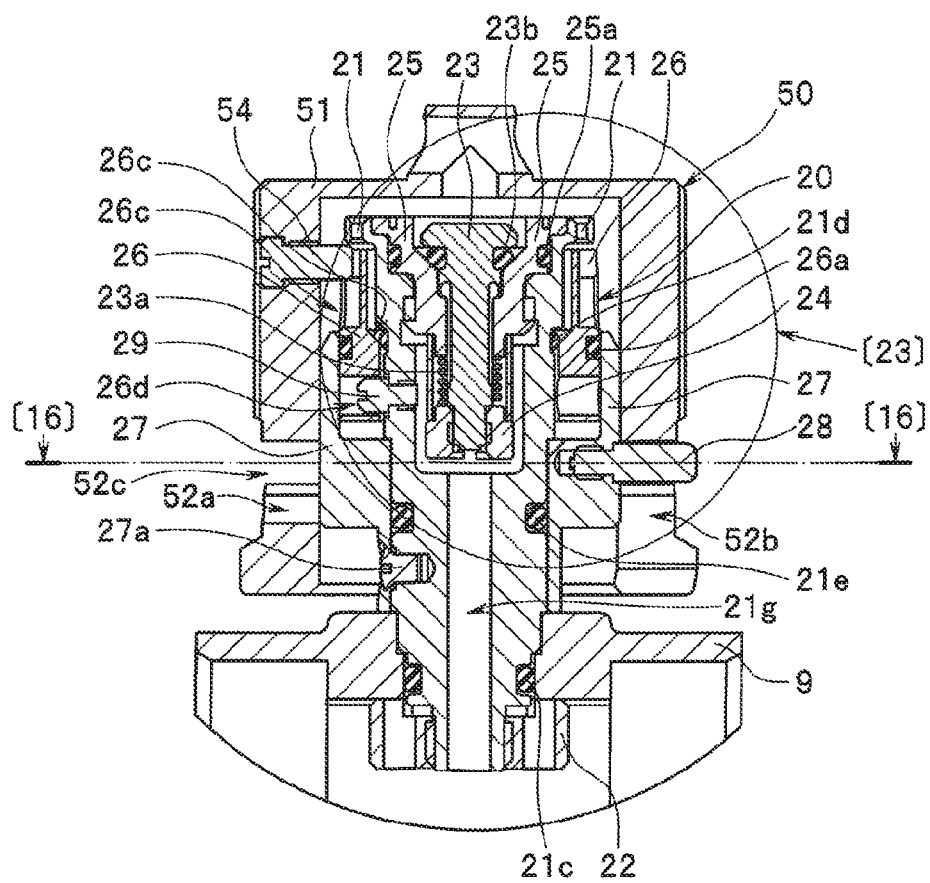
FIG. 9 is a sectional view taken along line [9]-[9] in FIG. 8.
Figure 10:
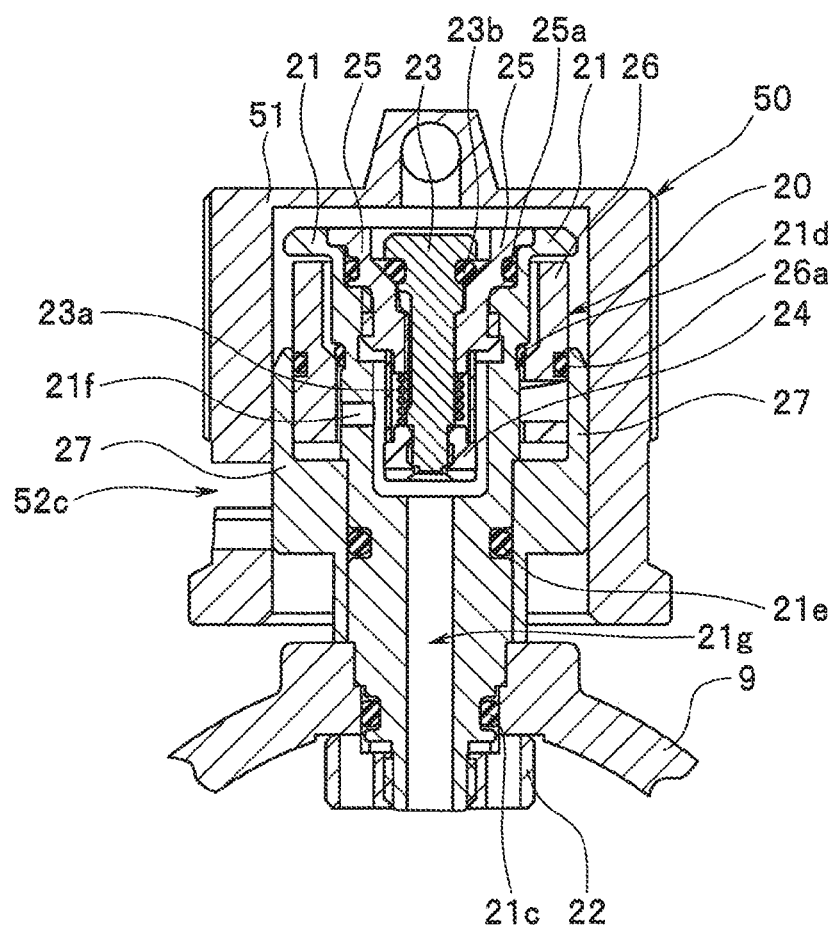
FIG. 10 is a sectional view taken along line [10]-[10] in FIG. 8.

FIG. 8 to FIG. 10 are figures showing a state in which the sterilization cap is attached to the check valve unit. Among the figures, FIG. 8 is a top view (during a closed state of a communication path). FIG. 9 is a side sectional view viewed from a direction orthogonal to the long axis of the light guide connector (a sectional view taken along line [9]-[9] in FIG. 8). FIG. 10 is a side sectional view viewed from the direction along the long axis of the light guide connector (a sectional view taken along line [10]-[10] in FIG. 8).

Figure 11:
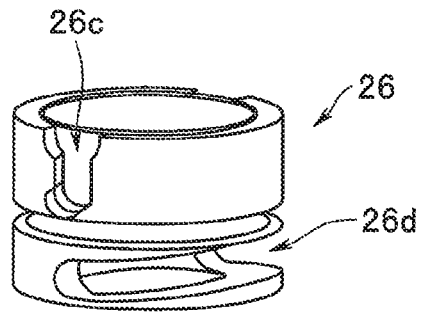
FIG. 11 is an exterior perspective view extracting and showing only a receiving ring among constituent members of the check valve unit in the endoscope in the first embodiment of the present invention.
Figure 12:
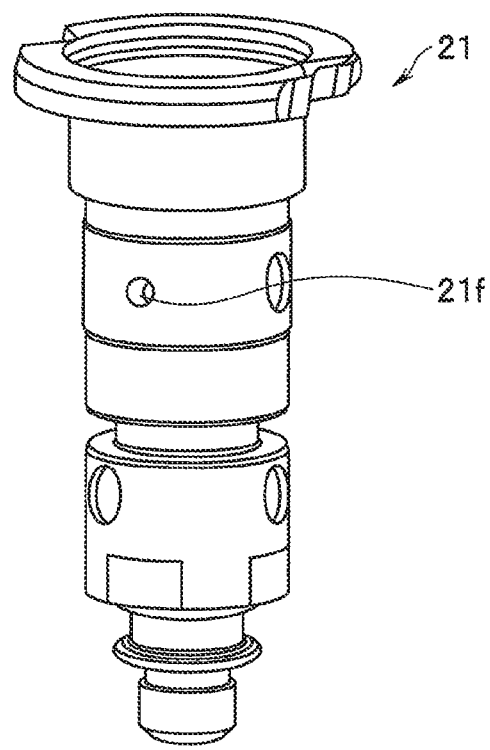
FIG. 12 is an exterior perspective view extracting and showing only a pipe sleeve main body section among the constituent members of the check valve unit in the endoscope in the first embodiment of the present invention.
Figure 13:
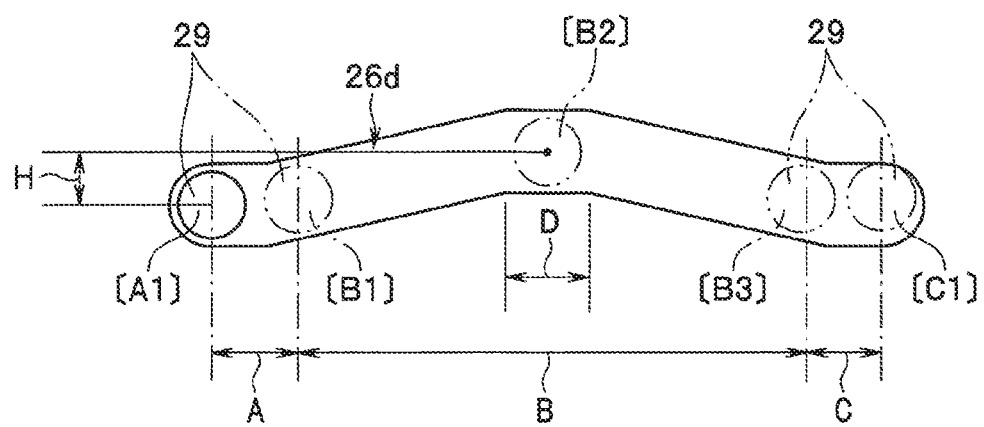
FIG. 13 is a development view enlarging and showing a cam shape of a cam groove formed in the receiving ring shown in FIG. 11.

FIG. 11 is an exterior perspective view extracting and showing only a receiving ring among constituent members of the check valve unit. FIG. 12 is an exterior perspective view extracting and showing only a pipe sleeve main body section 21 among the constituent members of the check valve unit. FIG. 13 is a development view enlarging and showing a cam shape of a cam groove formed in the receiving ring shown in FIG. 11.

First, schematic configurations of the check valve unit 20 and the sterilization cap 50 in the endoscope 1 in the present embodiment are explained with reference to the drawings.

As shown in FIG. 2 and the like, the check valve unit 20 is configured by constituent members such as the pipe sleeve main body section 21, a receiving ring 26, a reinforcing member 27, and a guide pin 28.

The pipe sleeve main body section 21 is configured from a cylindrical body including a communication hole 21*g*, which pierces through the pipe sleeve main body section 21 in a long axis direction and has openings at both ends, and formed in a substantially cylindrical shape as a whole. The pipe sleeve main body section 21 is disposed to project from an outer surface of the light guide connector 9 with a long axis of the pipe sleeve main body section 21 directed outward along a radial direction of the light guide connector 9. In this case, as explained below, the pipe sleeve main body section 21 is fixed to the light guide connector 9 by a pressing nut 22 (not shown in FIG. 2. See FIG. 4 and the like) from an inner side of the light guide connector 9. With such a configuration, the pipe sleeve main body section 21 is formed as a member that secures a communication state of an internal space and an external space of the light guide connector 9.

In other words, the pipe sleeve main body section 21 is implanted to pierce through a wall surface of the light guide connector 9 from the outer surface toward the inner side of the light guide connector 9. In this case, the light guide connector 9 functions as a partition wall that shields the internal space (an inner side space) of the endoscope 1 and the external space (an outer side space) of the endoscope 1. The pipe sleeve main body section 21 is coupled to the partition wall (i.e., the light guide connector 9) to be capable of being water tight (see, an O-shaped ring 21*c* in FIG. 9 explained below).

The communication hole 21*g* of the pipe sleeve main body section 21 is formed in a form piercing through the pipe sleeve main body section 21 and including the openings at both the ends. With this configuration, when the pipe sleeve main body section 21 is attached to be implanted in the light guide connector 9 (the partition wall), a communication hole 21*a* functions as a communication hole that communicates with the inner side space. The communication hole 21*a* is formed to include an internal wall surface. In an intermediate part in the long axis direction of the pipe sleeve main body section 21, as shown in FIG. 12, a communication opening 21*f*, which is a through-hole piercing through the pipe sleeve main body section 21, is drilled to communicate with the internal wall surface of the communication hole 21g from a part on an outer circumferential surface of the pipe sleeve main body section 21. As explained below, the communication opening 21f is an opening part that forms a part of a communication path [AR] other than a valve structure of the check valve unit 20 (details are explained below).

The receiving ring 26 is a first frame body opened at both ends, formed in a substantially annular frame shape as a whole, and disposed on an outer circumference side of the pipe sleeve main body section 21 and in a position that covers an outer surface close to an upper end. The receiving ring 26 is disposed to be capable of operating with respect to the pipe sleeve main body section 21. "Capable of operating" more specifically means that the receiving ring 26 is disposed to be movable in the long axis direction of the pipe sleeve main body section 21 and rotatable in a circumferential direction around the long axis. The receiving ring 26 is an opening/closing member by cooperating with the sterilization cap 50 to thereby open and close the communication path [AR] in the portion other than the valve structure of the check valve unit 20 (details are explained below. See FIG. 11 and the like).

The reinforcing member 27 is a second frame body formed in a substantially cylindrical frame shape, disposed to cover an outer surface of a part of a region close to a lower part of the pipe sleeve main body section 21 and a lower side outer circumferential surface of the receiving ring 26, and fixed to the pipe sleeve main body section 21 by a screw 27a. The reinforcing member 27 (the second frame body) is sheathed over the pipe sleeve main body section 21 (the cylindrical body) while keeping water tightness (see an O-shaped ring 21e in FIG. 9 explained below). The reinforcing member 27 (the second frame body) is sheathed over the receiving ring 26 (the first frame body) while keeping water tightness (see an O-shaped ring 26a in FIG. 9 explained below).

Between an inner side of the reinforcing member 27 and an outer side of the pipe sleeve main body section 21, as explained above, the receiving ring 26 is disposed to be movable in the long axis direction of the pipe sleeve main body section 21 and rotatable in the circumferential direction around the long axis. Opening and closing of a space between the receiving ring 26 and the pipe sleeve main body section 21 and a first space between the reinforcing member 27 and the pipe sleeve main body section 21 are switched by an operation of the receiving ring 26 (details are explained below). The space between the receiving ring 26 and the pipe sleeve main body section 21 communicates with the outer side space. The first space communicates with the inner side space via the communication opening 21f (the through-hole). Therefore, both the spaces form a part of the communication path [AR] that causes the internal space and the external space of the endoscope 1 to communicate with each other. The communication path [AR] is configured such that opening and closing are switched by the operation of the receiving ring 26.

The guide pin 28, which engages with (the guide groove 52 of) the sterilization cap 50, is projectingly provided on an outer circumferential surface of the reinforcing member 27 (the second frame body) with a long axis of the guide pin 28 directed to an outward radial direction. The guide pin 28 is a member that engages with (the guide groove 52 of) the sterilization cap 50 and prevents the sterilization cap 50 from coming off. That is, the sterilization cap 50 is formed to be attachable to the reinforcing member 27 (the second frame body).

That is, the sterilization cap 50 is mainly configured by a cap main body 51 formed to cover the check valve unit 20, formed in a substantially cylindrical shape as a whole, closed on one surface of the substantially cylindrical shape, and formed to have an opening on the other surface. The sterilization cap 50 is a lid member attached by being put over the check valve unit 20. FIG. 3 and FIG. 4 show a state in which the sterilization cap 50 is attached to the check valve unit 20.

In the cap main body 51 of the sterilization cap 50, a guide groove 52 for engaging with the guide pin 28 of the check valve unit 20 and preventing the sterilization cap 50 from coming off is formed. The guide groove 52 includes, as shown in FIG. 5 and the like, a lead-in section 52b (a base section) that extends from a lower end edge of the sterilization cap 50 upward in an axial direction of the sterilization cap 50, a guide section 52c (an intermediate section) that extends in a circumferential direction of the cap main body 51 while having a predetermined length and guides rotation of the sterilization cap 50, and a rotation restricting section 52a (an end portion) formed in a deepest end portion of the guide section 52c and formed in a concave shape downward in the axial direction of the sterilization cap 50 to restrict the rotation of the sterilization cap 50. The guide groove 52 is a through-groove continuously formed from the lead-in section 52b to the rotation restricting section 52a through the guide section 52c. Note that the guide groove 52 is formed on a circumferential surface along a rotating direction of the sterilization cap 50.

In the sterilization cap 50, as shown in FIG. 7 and the like, a shaft-like cam operation pin 54 is fixed from an internal wall surface of the sterilization cap 50 toward an inner side radial direction in a position close to the closed surface of the sterilization cap 50. The cam operation pin 54 is disposed to be capable of being locked in a fitting groove 26c (details are explained below. See FIG. 11) of the receiving ring 26 (the first frame body) when the sterilization cap 50 is attached to the check valve unit 20. The cam operation pin 54 is configured to rotate the receiving ring 26 (the first frame body) when, in that state, that is, a state in which the sterilization cap 50 is attached to the check valve unit 20 in a regular position, the sterilization cap 50 is rotated in a predetermined direction around a long axis of the check valve unit 20 (details are explained below).

A detailed configuration of the check valve unit 20 is explained mainly with reference to FIG. 8 to FIG. 13. As explained above, the check valve unit 20 is configured from the substantially cylindrical pipe sleeve main body section 21 and the like. The pipe sleeve main body section 21 is fixed to the light guide connector 9 by the pressing nut 22. In a coupling part of the pipe sleeve main body section 21 and the light guide connector 9, an O-shaped ring 21c that secures air tightness and water tightness between the pipe sleeve main body section 21 and the light guide connector 9 is disposed. The O-shaped ring 21c is attached to an outer circumference of the pipe sleeve main body section 21. Consequently, the pipe sleeve main body section 21 is coupled to the light guide connector 9 (the partition wall) to be capable of being water tight.

On an upper part side of the pipe sleeve main body section 21, the communication hole 21g is expanded in diameter. A valve supporting pipe sleeve 25 formed in a substantially annular shape is disposed in an inner side part of the communication hole 21g. A check valve 23 is inserted through and disposed in an inner side part of the valve supporting pipe sleeve 25. The check valve 23 is a check valve section including a valve mechanism that irreversibly performs ventilation from the internal space to the external space of the endoscope 1. The valve supporting pipe sleeve 25 is a constituent member that supports the check valve 23.

In other words, the valve supporting pipe sleeve 25, which is a valve body, includes the check valve 23, which is the check valve section that opens and closes according to a pressure difference between the internal space (the inner side space) and the external space (the outer side space) of the endoscope 1, and supports the check valve 23.

A spring retainer 24 is screwed at a lower end of the check valve 23. In this case, a spring 23a is externally inserted and disposed over an outer circumferential section of the check valve 23. The spring 23a is disposed between an upper surface of the spring retainer 24 and a lower surface of the valve supporting pipe sleeve 25. Consequently, the spring 23a urges the check valve 23 against the valve supporting pipe sleeve 25 toward the internal space side of the endoscope 1, that is, a downward side.

Note that an O-shaped ring 25a that secures air tightness and water tightness between the pipe sleeve main body section 21 (close to an inner circumference side upper end) and the valve supporting pipe sleeve 25 (close to an outer circumference side) are disposed between the pipe sleeve main body section 21 and the valve supporting pipe sleeve 25. The O-shaped ring 25a is attached to an outer circumference of the valve supporting pipe sleeve 25. Consequently, the valve body (the valve supporting pipe sleeve 25 including the check valve 23) is fixed to the communication hole 21g of the pipe sleeve main body section 21 while keeping water tightness via the O-shaped ring 25a.

An O-shaped ring 23b that secures air tightness and water tightness between the valve supporting pipe sleeve 25 (close to an inner circumference side upper end) and the check valve 23 (close to an outer circumference side upper end) are disposed between the valve supporting pipe sleeve 25 and the check valve 23. The O-shaped ring 23b is attached to an outer circumference of the check valve 23.

An O-shaped ring 21d that secures air tightness and water tightness between the pipe sleeve main body section 21 (close to an outer circumference side intermediate upper end) and the receiving ring 26 (the inner circumference side intermediate portion) is disposed between the pipe sleeve main body section 21 and the receiving ring 26. The O-shaped ring 21d is attached to the outer circumference of the pipe sleeve main body section 21. In a part on the receiving ring 26 side against which the O-shaped ring 21d is brought into press-contact, that is, a contact part on an inner circumferential surface side of the receiving ring 26, as shown in FIG. 9, FIG. 10, FIG. 19, FIG. 20, and FIG. 22 (more specifically, see FIG. 23, FIG. 24 and the like as well), a taper surface 26b inclining downward from an outer circumference side to an inner circumference side is formed. The taper surface 26b is formed in the contact part with the O-shaped ring 21d on the receiving ring 26 side, whereby a sealed state between the pipe sleeve main body section 21 and the receiving ring 26 is surely secured. At the same time, the taper surface 26b also has a shape for enabling easy shift to an open state when the sealed state between the pipe sleeve main body section 21 and the receiving ring 26 is released. The taper surface 26b and the O-shaped ring 21d are parts functioning as an opening/closing section that opens and closes the communication path [AR] at appropriate timing.

An O-shaped ring 26a that secures air tightness and water tightness between the receiving ring 26 (an outer circumference side intermediate portion) and the reinforcing member 27 (close to an inner circumference side upper end) is disposed between the receiving ring 26 and the reinforcing member 27. The O-shaped ring 26a is attached to an outer circumference of the receiving ring 26.

An O-shaped ring 21e that secures air tightness and water tightness between the pipe sleeve main body section 21 (an outer circumference side intermediate portion) and the reinforcing member 27 (close to an inner circumference side lower end) is disposed between the pipe sleeve main body section 21 and the reinforcing member 27. The O-shaped ring 21e is attached to the outer circumference of the pipe sleeve main body section 21.

As explained above, the O-shaped rings are disposed as appropriate in the respective predetermined parts on an inside of the check valve unit 20 and configured to secure air tight and water tight states between the internal respective constituent members.

In the check valve unit 20, in a normal state, the check valve 23 is urged toward the inner side of the endoscope 1 by an urging force of the spring 23a. At this point, the check valve 23 is in a state in which the O-shaped ring 23b is pressed against a taper portion of the valve supporting pipe sleeve 25. The check valve 23 is restricted to this position. The communication hole 21g of the pipe sleeve main body section 21 is in a seal state in which the communication hole 21g is hermetically sealed by the O-shaped ring 23b.

In this state, when pressure in the internal space of the endoscope 1 is higher than pressure in the external space, the check valve 23 is pushed upward in an external direction of the endoscope 1 resisting the urging force of the spring 23a. Consequently, a gap is formed between the check valve 23 and the valve supporting pipe sleeve 25 and the seal state by the O-shaped ring 23b is broken. Therefore, the communication hole 21g of the pipe sleeve main body section 21 is opened. Consequently, gas in the internal space of the endoscope 1 flows out to the external space. A difference between the pressure in the internal space of the endoscope 1 and the pressure (atmospheric pressure) in the external space decreases.

On the other hand, as explained above, on an outer circumference side close to an upper end of the pipe sleeve main body section 21, the receiving ring 26 having the substantially annular shape is disposed to be rotatable around the long axis with respect to the pipe sleeve main body section 21. As shown in FIG. 11, the receiving ring 26 is formed to include a fitting groove 26c and a cam groove 26d.

Of the grooves, the fitting groove 26c is a groove section with which the cam operation pin 54 of the sterilization cap 50 engages when the sterilization cap 50 is attached to the check valve unit 20. Therefore, the fitting groove 26c is formed as a bottomed groove that has an opening in an upper end ridge portion of the receiving ring 26 on an outer circumferential surface of the receiving ring 26 and extends from the upper end opening to an intermediate portion in an axial direction of the receiving ring 26.

Since a cam pin 29 of the pipe sleeve main body section 21 is slidably disposed, the cam groove 26d is a cam groove coupled to the cam pin 29. As shown in FIG. 11, the cam groove 26d is a through-groove extending in a circumferential direction along an outer circumferential surface close to a lower end of the receiving ring 26.

The cam pin 29 is a shaft-like member provided projecting outward in a radial direction (a direction orthogonal to the long axis) of the pipe sleeve main body section 21 from an outer circumferential surface of the pipe sleeve main body section 21 in an intermediate part in the long axis direction of the pipe sleeve main body section 21. As explained above, the receiving ring 26 is rotatably disposed on the outer circumference side close to the upper end of the pipe sleeve main body section 21. At this point, the cam pin 29 is coupled to the cam groove 26d of the receiving ring 26.

Therefore, with such a configuration, when the sterilization cap 50 is attached to the check valve unit 20 in a regular position, the cam operation pin 54 fits in the fitting groove 26c. In this state, when the sterilization cap 50 is rotated in a predetermined direction around the long axis of the check valve unit 20, the cam operation pin 54 acts on the fitting groove 26c and rotates the receiving ring 26 in the same direction. When the receiving ring 26 is rotated in the predetermined direction in this way, since the cam pin 29 is coupled to the cam groove 26d, the receiving ring 26 moves in a long axis direction of the pipe sleeve main body section 21 according to a groove shape of the cam groove 26d. That is, the receiving ring 26 moves up and down in the long axis direction of the pipe sleeve main body section 21 to thereby open and close the communication path [AR] in the portion other than the valve structure of the check valve unit 20. Before explaining details of the action, the groove shape of the cam groove 26d is explained.

For example, as shown in FIG. 13, the cam groove 26d is formed to have a substantially reverse V-shape as a whole. That is, an intermediate portion in a substantially center portion of the cam groove 26d is formed in the substantially reverse V-shape toward the long axis direction of the check valve unit 20 (upward). Note that length in the circumferential direction of the intermediate portion (a region B) of the cam groove 26d is formed to be larger than length of a start point portion or an end point portion.

The cam groove 26d is formed to include, in both end portions (the start point portion and the end point portion) and the substantially center portion (the intermediate portion), regions (regions indicated by signs A, D, and C in FIG. 13) parallel to a horizontal direction (a circumferential direction of the receiving ring 26) and having a predetermined length. Note that a form is desirable in which the cam groove 26d is formed line-symmetrically with respect to a substantially center part of the region indicated by sign D in the example shown in FIG. 13.

Details of action in a process for attaching and detaching the sterilization cap 50 to and from the check valve unit 20 are explained below. In that case, when the receiving ring 26 rotates according to the rotation of the sterilization cap 50, the receiving ring 26 secures a sealed state of the communication path [AR] of the check valve unit 20 when the cam pin 29 is present in the region indicated by sign A (the start point portion). Subsequently, when the cam pin 29 shifts to the region indicated by sign B (the intermediate portion), the receiving ring 26 brings the communication path [AR] into an open state according to action of the cam pin 29 and the cam groove 26d. At this point, the open state of the communication path [AR] by the receiving ring 26 is maximized in the region indicated by sign D, that is, a vertex part of the cam groove 26d. Subsequently, when the cam pin 29 shifts to the region indicated by sign C (the end point portion), the receiving ring 26 secures the sealed state of the communication path [AR] of the check valve unit 20 again.

In other words, when the cam pin 29 is located in the region A (the start point portion) or the region C (the end point portion), a space between the first space and the outer side space is in a shielded state. On the other hand, when the cam pin 29 is located in the intermediate portion, a space between the first space and the outer side space is opened.

Figure 14:
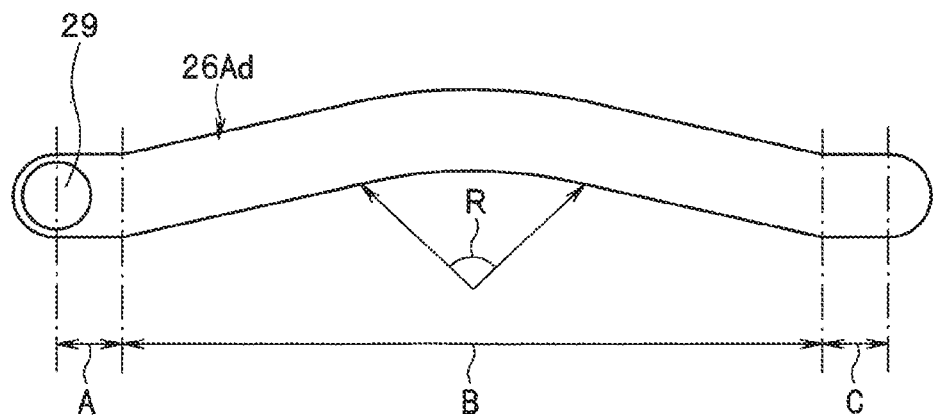
FIG. 14 is a development view showing a first modification concerning the cam groove shown in FIG. 13.
Figure 15:
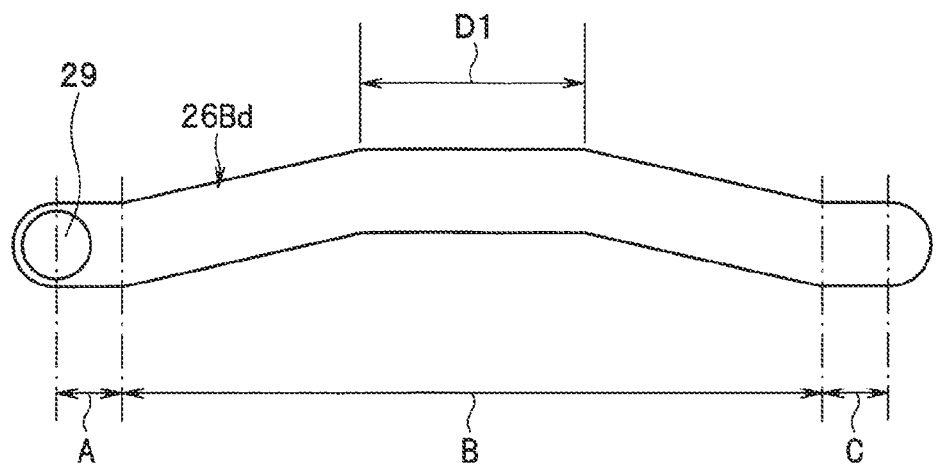
FIG. 15 is a development view showing a second modification concerning the cam groove shown in FIG. 13.

Action of the receiving ring 26 at the time when the sterilization cap 50 is attached to the check valve unit 20 and the sterilization cap 50 is rotated can be controlled by contriving the groove shape of the cam groove 26d. Therefore, the groove shape of the cam groove 26d is not limited to the illustration in FIG. 13 and may be other forms. For example, FIG. 14 and FIG. 15 show two modifications concerning the cam groove 26d formed in the receiving ring 26 in the check valve unit 20 of the endoscope 1 in the present embodiment. Details of the two modifications are explained below.

On the other hand, the reinforcing member 27 formed in a substantially cylindrical shape is disposed in a part that covers (a circumferential surface of the cam groove 26d of) the lower side outer circumferential surface of the receiving ring 26 and covers an outer circumferential surface of a part of a region close to a lower part of the pipe sleeve main body section 21. The reinforcing member 27 is fixed on the outer circumferential surface of the pipe sleeve main body section 21 by a fastening member such as the screw 27a. As explained above, on the outer circumferential surface of the reinforcing member 27 (the second frame body), the guide pin 28 having the shaft shape is implanted to project outward along a radial direction of the reinforcing member 27, that is, a direction orthogonal to the long axis direction of the check valve unit 20. The guide pin 28 is provided to, when the sterilization cap 50 is attached to the check valve unit 20, by being engaged and received in the guide groove 52 of the sterilization cap 50, guide the rotation of the sterilization cap 50 and prevent the sterilization cap 50 from coming off through engagement with the guide groove 52. In other words, the guide pin 28 is relatively disposed in a predetermined position in the guide groove 52 according to the rotation of the sterilization cap 50.

The check valve unit 20 configured as explained above includes a check valve structure that irreversibly performs ventilation from the internal space to the external space of the endoscope 1 and, at the same time, has a function of a ventilation valve that opens and closes the communication path [AR] of the portion other than the valve structure of the check valve unit 20 and causes the internal space and the external space of the endoscope 1 to communicate with each other in a process for attaching and detaching the sterilization cap 50 to and from the check valve unit 20.

An overview of action in the process for attaching and detaching the sterilization cap 50 to and from the check valve unit 20 is explained. After attaching the sterilization cap 50 to the check valve unit 20, when a user rotates the sterilization cap 50 in the predetermined direction, the receiving ring 26 rotates in the same direction according to the rotation of the sterilization cap 50. When the receiving ring 26 rotates, the receiving ring 26 moves downward along the long axis direction of the check valve unit 20 according to action of the cam pin 29 on the check valve unit 20 side and the cam groove 26d on the receiving ring 26 side. Consequently, a gap (see FIG. 19, FIG. 24, and the like) is formed between an inner circumferential surface of the receiving ring 26 and the outer circumferential surface of the pipe sleeve main body section 21. The gap is located in a part along the outer circumferential surface of the pipe sleeve main body section 21. The communication opening 21f communicating with the communication hole 21g is drilled on the outer circumferential surface of the pipe sleeve main body section 21. Therefore, the communication path

[AR] (see FIG. 23 and FIG. 24) that causes the internal space and the external space of the endoscope 1 to communicate with each other is formed.

When the sterilization cap 50 is further rotated in the same direction from this state, the receiving ring 26 moves upward along the long axis direction of the check valve unit 20 and returns to an original position. Consequently, the communication path [AR] returns to the closed state again.

After the sterilization cap 50 is attached to the check valve unit 20 in this way, in that state, the endoscope 1 is placed in an autoclave sterilization treatment apparatus and sterilization treatment is started. After predetermined sterilization treatment ends, the endoscope 1 is taken out from the autoclave sterilization treatment apparatus and the sterilization cap 50 is detached from the check valve unit 20. A procedure in detaching the sterilization cap 50 is possible by performing a procedure substantially opposite to a procedure during the attachment of the sterilization cap 50 explained above.

Action in attaching and detaching the sterilization cap 50 to and from the check valve unit 20 in the endoscope 1 in the present embodiment is explained in detail below with reference to FIG. 8 to FIG. 10, FIG. 13, and FIG. 16 to FIG. 24.

Figure 16:
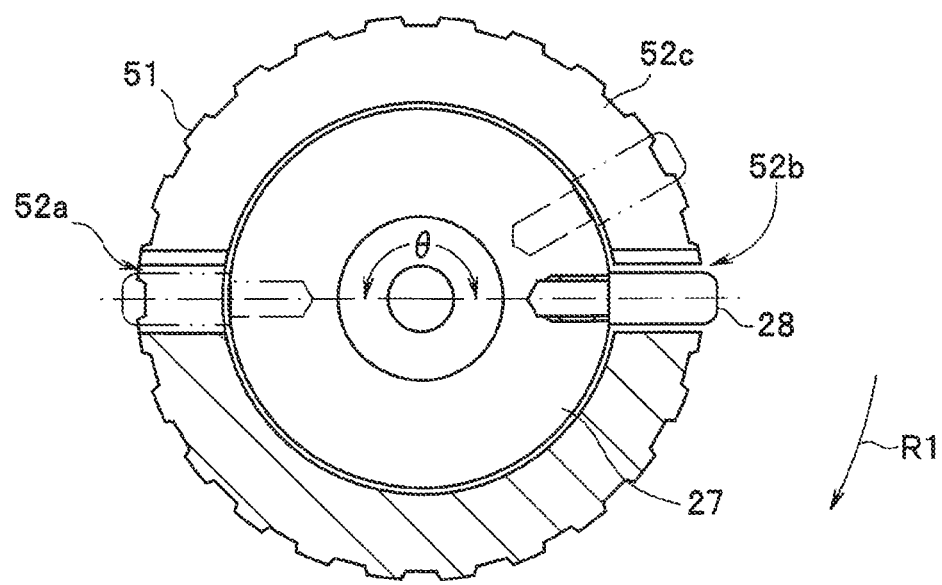
FIG. 16 is a diagram for explaining action at the time when the sterilization cap is attached to and detached from the check valve unit in the endoscope in the first embodiment of the present invention and is a sectional view taken along line [16]-[16] in FIG. 9 showing a positional relation of a guide pin of the check valve unit with respect to the guide groove of the sterilization cap.
Figure 17:
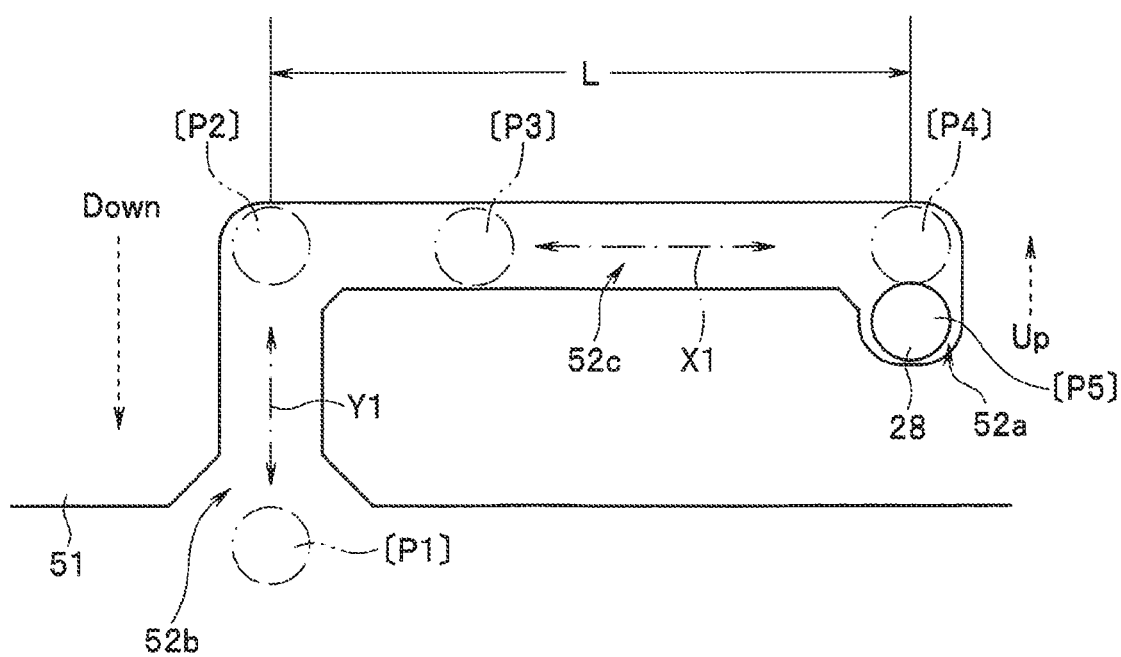
FIG. 17 is a conceptual diagram showing, in development, the guide groove of the sterilization cap shown in FIG. 16.

FIG. 16 and FIG. 17 are figures for explaining an overview of action at the time when the sterilization cap 50 is attached to and detached from the check valve unit 20 in the endoscope 1 in the present embodiment. That is, in a process for attaching and detaching the sterilization cap 50 to and from the check valve unit 20, a positional relation between the sterilization cap 50 and the check valve unit 20 at the time when the guide pin 28 of the check valve unit 20 moves relatively to the guide groove 52 of the sterilization cap 50 is shown. Note that FIG. 16 is a sectional view taken along line [16]-[16] in FIG. 9. FIG. 17 is a conceptual diagram showing, in development, a guide groove of the sterilization cap 50.

Figure 18:
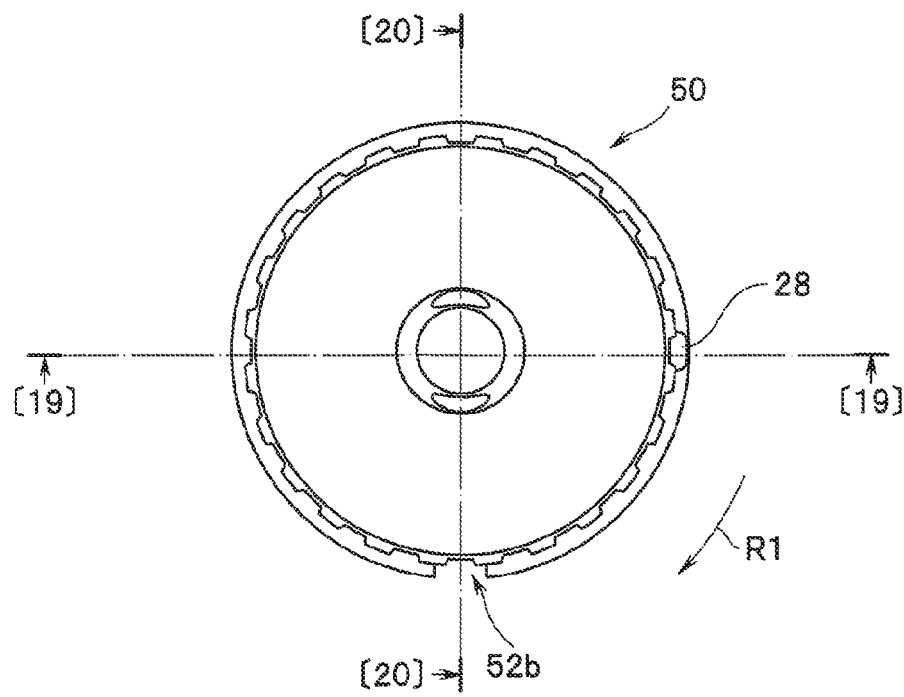
FIG. 18 is a top view showing action at the time when the sterilization cap is rotated by a predetermined rotation amount (θ=90 degrees) from the state shown in FIG. 8.
Figure 19:
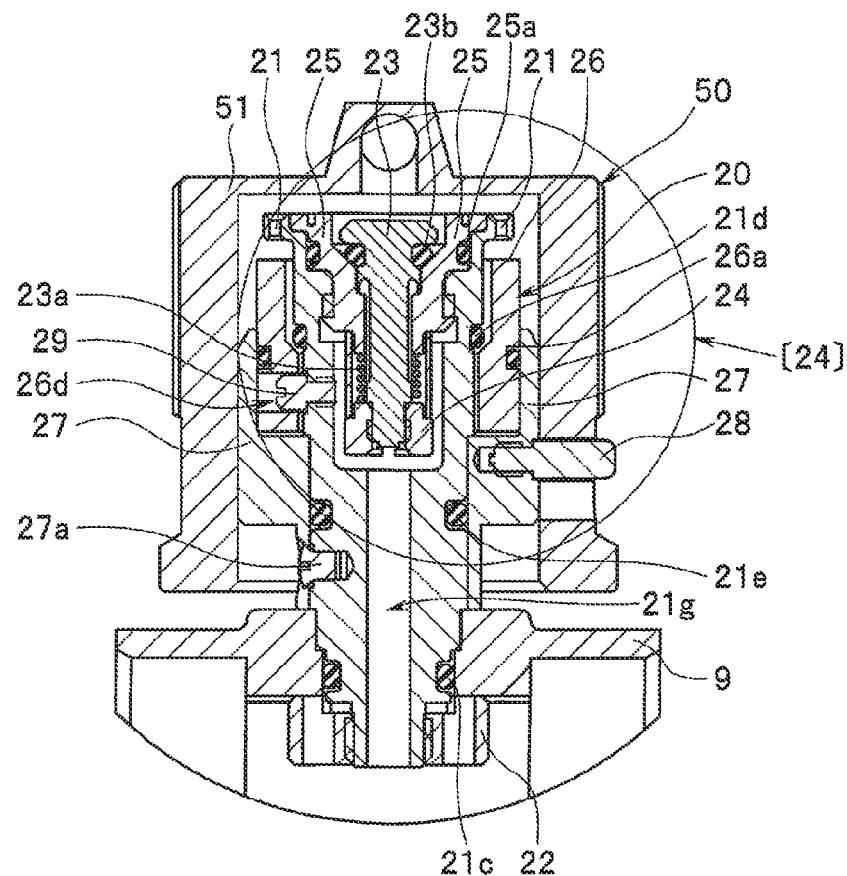
FIG. 19 is a sectional view taken along line [19]-[19] in FIG. 18.
Figure 20:
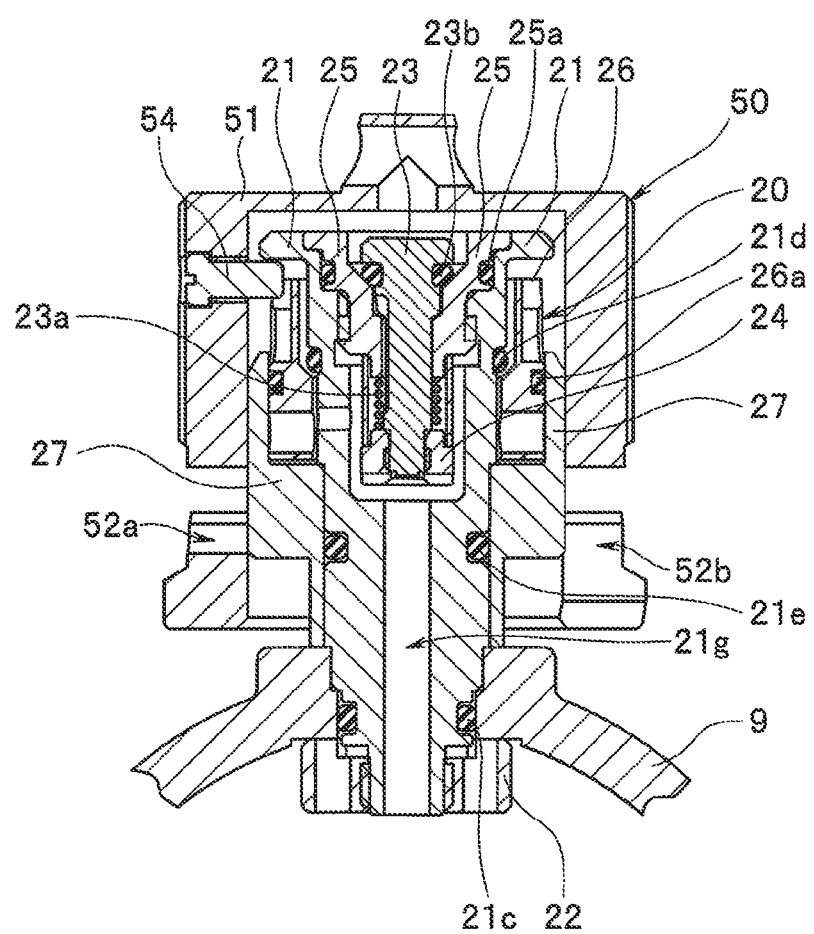
FIG. 20 is a sectional view taken along line [20]-[20] in FIG. 18.

FIG. 18 to FIG. 20 are figures showing a state at the time when the sterilization cap is rotated by a predetermined rotation amount (θ=90 degrees) from the state shown in FIG. 8 to FIG. 10 to bring the communication path [AR] of the check valve unit into the open state. Among the figures, FIG. 18 is a top view (during the open state of the communication path). FIG. 19 is a side sectional view (a sectional view taken along line [19]-[19] in FIG. 18) viewed from the direction orthogonal to the long axis of the light guide connector. FIG. 20 is a side sectional view (a sectional view taken along line [20]-[20] in FIG. 18) viewed from the direction along the long axis of the light guide connector.

Figure 21:
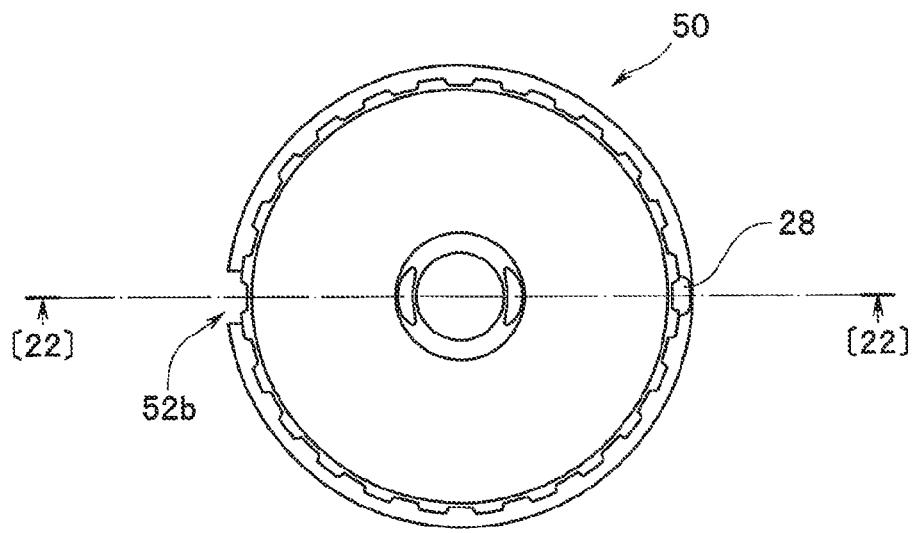
FIG. 21 is a top view showing action at the time when the sterilization cap is rotated by a predetermined rotation amount (θ=180 degrees) from the state shown in FIG. 8 and the sterilization cap is completely attached.
Figure 22:
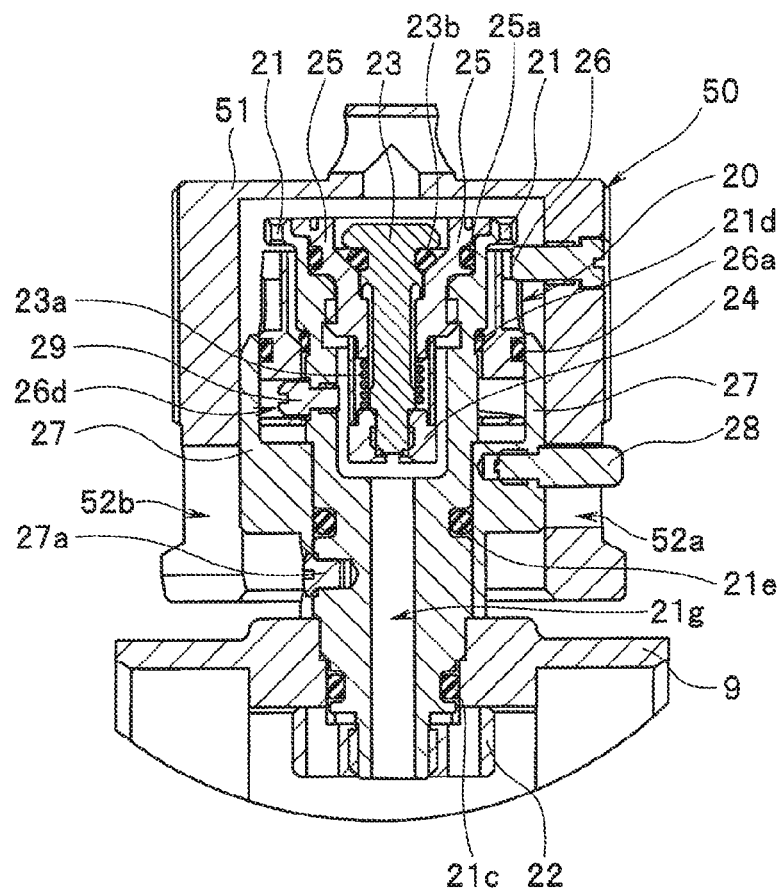
FIG. 22 is a sectional view taken along line [22]-[22] in FIG. 21.
Figure 23:
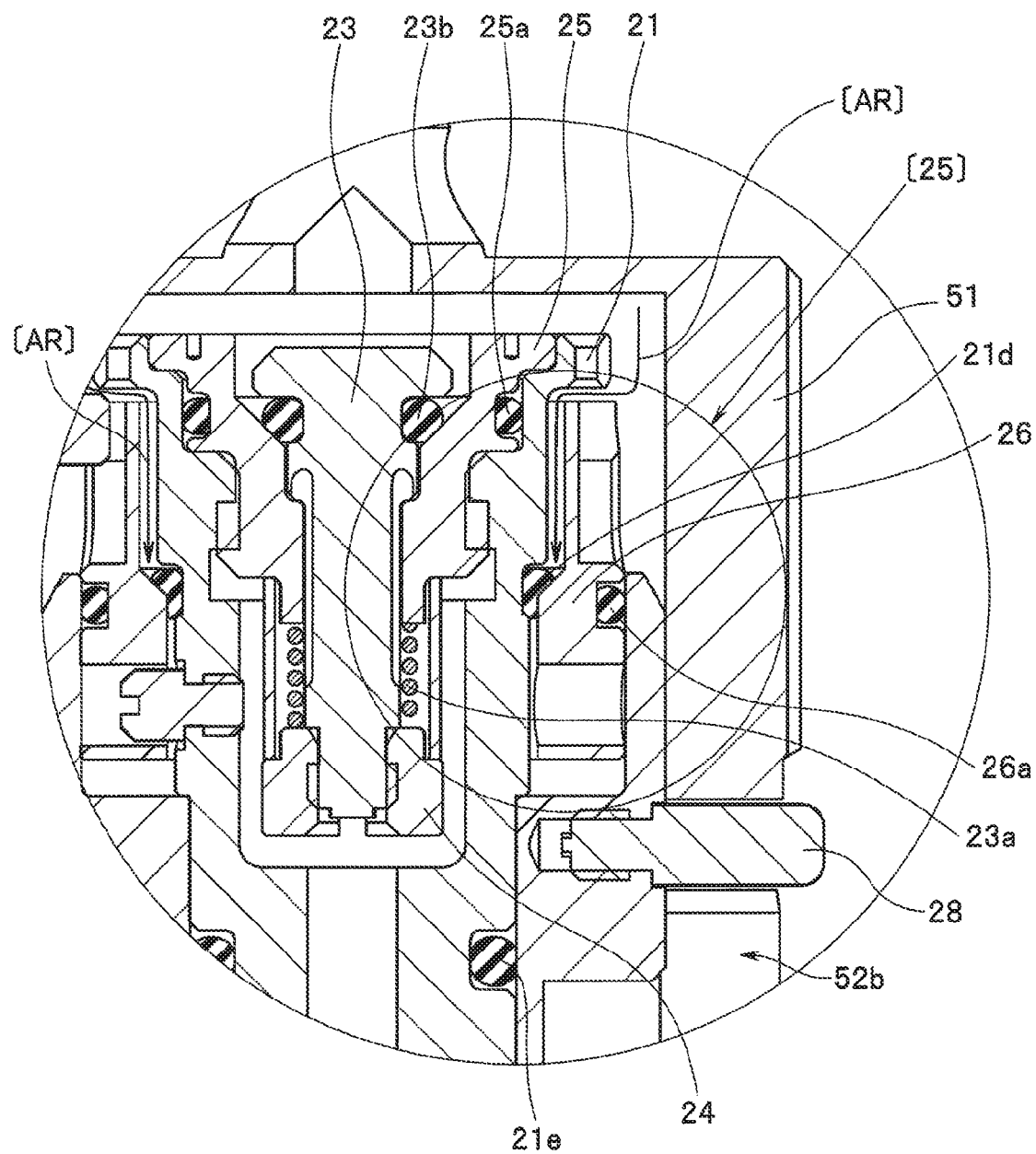
FIG. 23 is a main part enlarged view of a portion indicated by sign [23] in FIG. 9.
Figure 24:
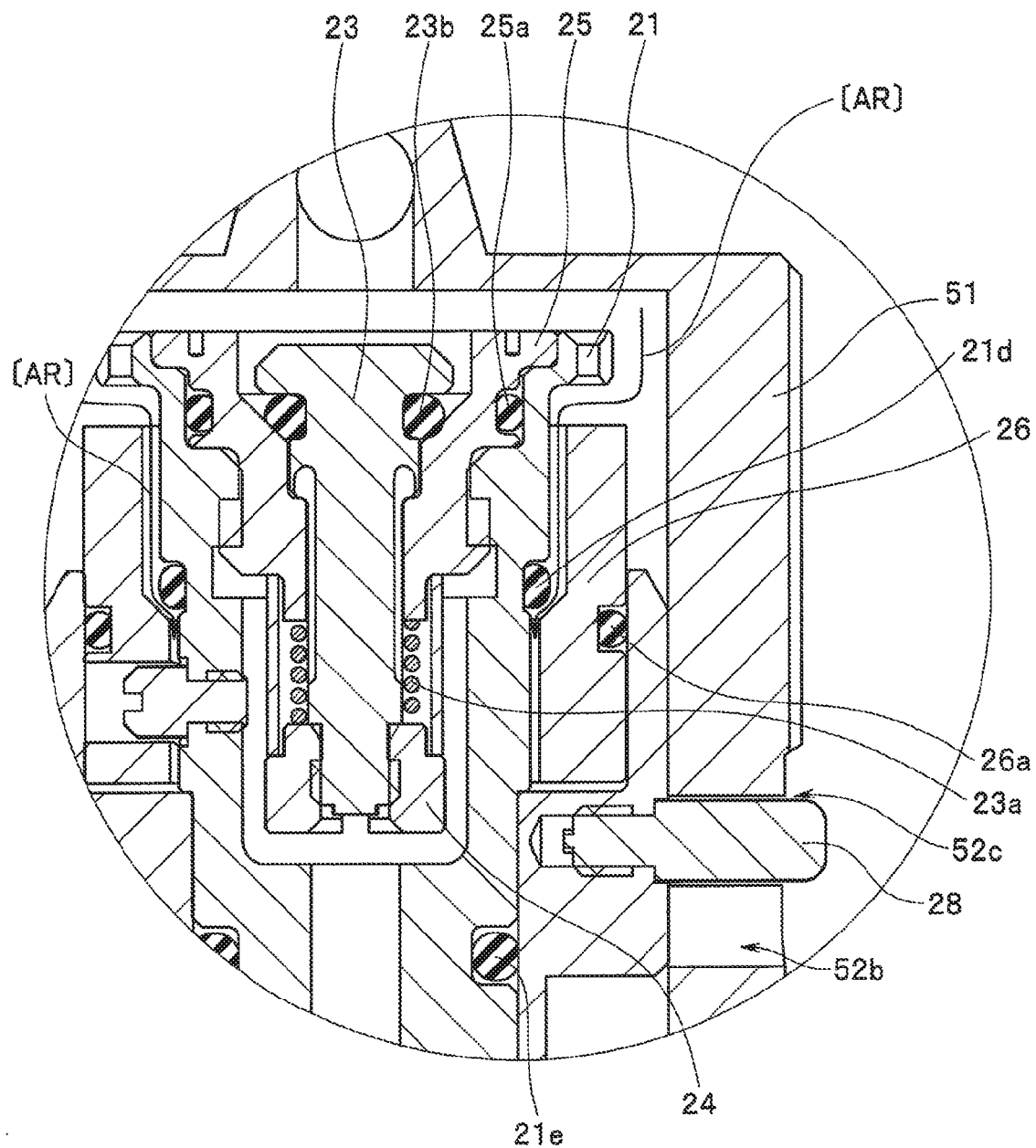
FIG. 24 is a main part enlarged view of a portion indicated by sign [24] in FIG. 19.

FIG. 21 and FIG. 22 are figures showing a state at the time when the sterilization cap is rotated by a predetermined rotation amount (θ=180 degrees) from the state shown in FIG. 8 and FIG. 9 to completely attach the sterilization cap. Note that, at this point, the communication path [AR] of the check valve unit is in the closed state again. Of the figures, FIG. 21 is a top view (during the closed state of the communication path). FIG. 22 is a side sectional view (a sectional view taken along line [22]-[22] in FIG. 21) viewed from the direction orthogonal to the long axis of the light guide connector. Note that FIG. 23 is a main part enlarged view of a portion indicated by sign [23] in FIG. 9. FIG. 24 is a main part enlarged view of a portion indicated by sign [24] in FIG. 19.

When the endoscope 1 in the present embodiment is set in, for example, the autoclave sterilization treatment apparatus, as in the past, the sterilization cap 50 is attached to the check valve unit 20 (see FIG. 2 to FIG. 4).

In this case, first, as shown in FIG. 8, FIG. 16, and FIG. 17, the user aligns the lead-in section 52b of the guide groove 52 of the sterilization cap 50 and the guide pin 28 of the check valve unit 20 and engages the guide pin 28 along the lead-in section 52b. That is, the user moves the sterilization cap 50 in a downward direction (an arrow Down direction in FIG. 17). At this point, the guide pin 28 relatively moves in a direction along an arrow Y1 in FIG. 17 from a position indicated by sign [P1] in FIG. 17 to a position indicated by sign [P2] in the figure. When the guide pin 28 reaches an end portion (the position of sign [P2]) of the lead-in section 52b, the movement in the downward direction (the arrow Down direction) of the sterilization cap 50 is restricted. At this point, as shown in FIG. 9, the cam operation pin 54 of the sterilization cap 50 simultaneously fits in the fitting groove 26c of the receiving ring 26.

The sterilization cap 50 is rotated in a predetermined direction, for example, an arrow R1 direction in FIG. 8 and FIG. 16 from this state. Then, the guide pin 28 relatively moves from the position indicated by sign [P2] in FIG. 17 to a position indicated by sign [P4] in the figure through a position indicated by sign [P3] in the figure in the horizontal direction (direction along an arrow X1 in FIG. 17) along the guide section 52c. When the guide pin 28 reaches an end portion (the position of sign [P4]) of the guide section 52c, the rotation of the sterilization cap 50 is restricted. The sterilization cap 50 is moved in an upward direction (an arrow Up direction in FIG. 17) from this state. Then, the guide pin 28 fits in the rotation restricting section 52a of the guide groove 52. Consequently, the sterilization cap 50 is attached to the check valve unit 20.

As explained above, when the sterilization cap 50 is rotated and the guide pin 28 is fit in the guide section 52c of the guide groove 52, movement in an up-down direction of the sterilization cap 50 is restricted. As a result, the sterilization cap 50 is prevented from coming off. In this state, since the cam operation pin 54 is fit in the fitting groove 26c, when the sterilization cap 50 is rotated, the receiving ring 26 rotates in the same direction.

As explained above, in the check valve unit 20, the cam pin 29 of the pipe sleeve main body section 21 is coupled to the cam groove 26d of the receiving ring 26 (see FIG. 9 and the like). In a state before the sterilization cap 50 is attached to the check valve unit 20, the cam pin 29 is present in, for example, a position indicated by sign [A1] in FIG. 13 (a start point portion) in the cam groove 26d. At this point, the guide pin 28 is present in the lead-in section 52b (a base section) of the guide groove 52. As shown in FIG. 9 and FIG. 10, the check valve unit 20 secures, with the valve structure of the check valve unit 20, a sealed state of the inside and the outside of the endoscope 1. At this point, a sealed state is secured by the O-shaped ring 21d between the pipe sleeve main body section 21 and the receiving ring 26. Consequently, in the state at this point, the communication path [AR] explained below is also in a closed state (see, in particular, FIG. 23).

In a closed state in which the cam pin 29 is present in the sign [A1] position in FIG. 13 in the cam groove 26d, when the user rotates the sterilization cap 50 in a predetermined direction, the receiving ring 26 rotates in the same direction according to the rotation of the sterilization cap 50. Then, the cam pin 29 moves relatively to the sterilization cap 50 and reaches a position indicated by sign [B1] in FIG. 13. In a region from sign [A1] to sign [B1] in FIG. 13, that is, a region indicated by sign A in the figure, the cam pin 29 only moves a predetermined distance in the horizontal direction (the circumferential direction) relatively to the sterilization cap 50. Therefore, in a period of the movement in region A, the cam pin 29 does not act on the cam groove 26*d*. That is, in this period, the closed state of the check valve unit 20 is maintained.

Subsequently, similarly, when the sterilization cap 50 is rotated in the same direction and the receiving ring 26 rotates in the same direction, the cam pin 29 relatively moves from the sign [B1] position in FIG. 13 to a sign [B2] position (a substantially vertex part) in the figure in the cam groove 26*d*. When the cam pin 29 is located in the region B (the intermediate portion) of the cam groove 26*d*, the guide pin 28 is located in the guide section 52*c* (the intermediate portion) of the guide groove 52. The cam groove 26*d* is formed as an inclined groove facing upward in a period from the sign [B1] position to the sign [B2] position in FIG. 13. As explained above, the cam pin 29 is actually fixed to the side surface of the pipe sleeve main body section 21. Therefore, when the cam pin 29 relatively moves along the upward inclined groove of the cam groove 26*d*, the receiving ring 26 provided with the cam groove 26*d* moves downward along the long axis direction of the pipe sleeve main body section 21. A movement amount of the receiving ring 26 in the long axis direction at this point is equal to a height dimension of a right angled triangle having inclination of the cam groove 26*d* as an oblique side, that is, sign H in FIG. 13. That is, in a region where the cam pin 29 reaches from the sign [B1] position to the sign [B2] position in FIG. 13, that is, a former half part of the region indicated by sign B in the figure, as the cam pin 29 relatively moves along the cam groove 26*d*, the receiving ring 26 moves by a predetermined amount H downward along the long axis direction of the check valve unit 20 (the pipe sleeve main body section 21). In this way, a state after the cam pin 29 relatively moves from the sign [B1] position to the sign [B2] position in FIG. 13 and the receiving ring 26 moves by the predetermined amount H is shown in FIG. 18 to FIG. 20 and FIG. 24.

As shown in FIG. 18, at this point, the sterilization cap 50 rotates by a rotation angle θ=90 degrees from the state shown in FIG. 8. As shown in FIG. 24 and the like, the receiving ring 26 moves downward in the axial direction by the predetermined amount H and a gap is formed between the pipe sleeve main body section 21 by the O-shaped ring 21*d* and the taper surface 26*b* of the receiving ring 26. Consequently, the communication path [AR] formed between the pipe sleeve main body section 21 and the taper surface 26*b* changes to the open state. The communication path [AR] communicates with the communication hole 21*g* of the pipe sleeve main body section 21 from the outer circumferential surface of the pipe sleeve main body section 21 via the communication opening 21*f*. Therefore, in this state, the internal space and the external space of the endoscope 1 communicate with each other via the communication path [AR].

Note that the cam groove 26*d* is formed to extend in the horizontal direction (the circumferential direction) by a predetermined length before and after the vertex part of sign [B2] in FIG. 13, that is, the region D. As explained above, when the cam pin 29 is located in the [B2] position of the cam groove 26*d*, the open state of the communication path [AR] by the receiving ring 26 is maximized. The region D is a region in which the [B2] position is extended in the horizontal direction. Therefore, such provision of the horizontal region D is an idea for temporarily maintaining the open state of the communication path [AR] in the attachment and detachment process of the sterilization cap 50.

Subsequently, similarly, when the sterilization cap 50 is rotated in the same direction and the receiving ring 26 rotates in the same direction, the cam pin 29 relatively moves from the sign [B2] position in FIG. 13 to a sign [B3] position in the figure in the cam groove 26*d*. The cam groove 26*d* is formed as an inclined groove facing downward in a period from the sign [B2] position to the sign [B3] position in FIG. 13. As explained above, the cam pin 29 is actually fixed to the side surface of the pipe sleeve main body section 21. Therefore, when the cam pin 29 relatively moves along the downward inclined groove of the cam groove 26*d*, the receiving ring 26 provided with the cam groove 26*d* moves upward along the long axis direction of the pipe sleeve main body section 21. A movement amount of the receiving ring 26 in the long axis direction at this point is equal to sign H in FIG. 13. In a region where the cam pin 29 reaches from the sign [B2] position to the sign [B3] position in FIG. 13, that is, a latter half part of the region indicated by sign B in the figure, as the cam pin 29 relatively moves along the cam groove 26*d*, the receiving ring 26 moves by the predetermined amount H upward along the long axis direction of the check valve unit 20 (the pipe sleeve main body section 21). Action in this period is substantially the same as the action of the receiving ring 26 during the movement of the cam pin 29 from the [B1] position to the [B2] position in FIG. 13 except that a moving direction is different. A state after the cam pin 29 relatively moves from the sign [B2] position to the sign [B3] position in FIG. 13 and the receiving ring 26 moves by the predetermined amount H is as shown in FIG. 22. At this point, the receiving ring 26 moves upward in the axial direction by the predetermined amount H and a space between the pipe sleeve main body section 21 and the taper surface 26*b* of the receiving ring 26 are sealed by the O-shaped ring 21*d*. Consequently, the communication path [AR] formed between the pipe sleeve main body section 21 and the taper surface 26*b* changes to the closed state. Therefore, at this point, the internal space and the external space of the endoscope 1 via the communication path [AR] is sealed.

After the cam pin 29 reaches the sign [B3] position in FIG. 13 in the cam groove 26*d* and brings the communication path [AR] into the closed state, when the user further rotates the sterilization cap 50 in the predetermined direction, the cam pin 29 reaches from the sign [B3] position to a sign [C1] position in FIG. 13. When the cam pin 29 is located in the region C (the end point portion) of the cam groove 26*d*, the guide pin 28 is located in the rotation restricting section 52*a* (the end portion) of the guide groove 52. In a region reaching from sign [B3] to sign [C1] in FIG. 13, that is, the region indicated by sign C in the figure, as in the sign A region in the figure, the cam pin 29 only moves a predetermined distance in the horizontal direction (the circumferential direction) relatively to the sterilization cap 50. Therefore, in a period of the movement in region C, the cam pin 29 does not act on the cam groove 26*d*. That is, in this period, the closed state of the check valve unit 20 is maintained. The sterilization cap 50 changes to a state shown in FIG. 21 in which the sterilization cap 50 rotates by a rotation angle θ=90 degrees from the state shown in FIG. 18 and rotates by a rotation angle θ=180 degrees from the state shown in FIG. 8.

In this way, the sterilization cap 50 is completely attached to the check valve unit 20. At this point, the internal space and the external space of the endoscope 1 are in the sealed state by the check valve unit 20 and the communication path [AR] is also in the closed state.

In this state, the endoscope 1 is placed in the autoclave sterilization treatment apparatus and autoclave sterilization treatment is started. At this point, first, an inside of the autoclave sterilization treatment apparatus changes to a negative pressure. Consequently, the internal space of the endoscope 1 changes to a positive pressure with respect to the inside of the autoclave sterilization treatment apparatus. In order to substantially equalize the pressures in the autoclave sterilization treatment apparatus and the endoscope 1, the check valve 23 of the check valve unit 20 moves upward and air in the internal space of the endoscope 1 is discharged. Consequently, pressure in the internal space and pressure in the external space of the endoscope 1 are equalized. At this point, the inside of the autoclave sterilization treatment apparatus has a negative pressure with respect to the external space. The internal space of the endoscope 1 changes to a negative pressure state equivalent to the negative pressure state in the autoclave sterilization treatment apparatus. Then, the check valve 23 returns to an original position with the urging force of the spring 23*a*. The check valve unit 20 changes to the sealed state. Steam and the like are prevented from entering the internal space of the endoscope 1. Sterilization treatment is applied in this state.

After the sterilization treatment ends, the inside of the autoclave sterilization treatment apparatus changes to a normal pressure or pressurized state equivalent to the atmospheric pressure again. At this point, the internal space of the endoscope 1 is in the negative pressure state.

After the endoscope 1 is taken out from the autoclave sterilization treatment apparatus, the sterilization cap 50 is taken out from the check valve unit 20. A procedure for detaching the sterilization cap 50 is opposite to the procedure for attaching the sterilization cap 50 to the check valve unit 20.

That is, the user rotates the sterilization cap 50 in a direction opposite to the direction in which the sterilization cap 50 is attached. In the closed state during the attachment, the cam pin 29 is present in the [C1] position in FIG. 13 of the cam groove 26*d*. The closed state of the check valve unit 20 and the communication path [AR] is maintained from the [C1] position to the [B3] position (in the region C). Subsequently, the communication path [AR] gradually changes to the open state from the [B3] position to the [B2] position and changes to the maximum open state in the [B2] position. Thereafter, the communication path [AR] gradually changes to the closed state from the [B2] position to the [B1] position. The closed state is secured from the [B1] position to the [A1] position.

In this way, in the process for detaching the sterilization cap 50, since the communication path [AR] changes to the open state, air enters the internal space of the endoscope 1 from the external space through the communication path [AR]. Therefore, the internal space of the endoscope 1 changes to a pressure state substantially the same as the atmospheric pressure in the external space. When the sterilization cap 50 is completely detached from the check valve unit 20, air tight and water tight states are maintained in the internal space of the endoscope 1 by the valve structure of the check valve unit 20.

Note that the guide groove 52 of the sterilization cap 50 is formed to have a predetermine angle θ in the circumferential direction. The angle θ coincides with a rotatable angle of the sterilization cap 50. In the present embodiment, the rotatable angle of the sterilization cap 50 is set to, for example, θ=180 degrees (see FIG. 16).

As a moving distance (length L of the guide section 52*c*; see FIG. 17) involved in the rotation of the sterilization cap 50, a distance L of approximately ½ of a circumferential length of the sterilization cap 50 is set. Therefore, the receiving ring 26 is configured to move in the up-down direction for time substantially proportional to a relative moving distance of the cam pin 29 involved in the rotation of the sterilization cap 50 to gradually perform the opening and closing of the communication path [AR].

Note that, in the first embodiment explained above, an example is explained in which the groove shape of the cam groove 26*d* of the receiving ring 26 in the check valve unit 20 is formed in the substantially reverse V-shape as shown in FIG. 13. As explained above, the groove shape of the cam groove 26*d* is means for controlling action of the receiving ring 26 at the time when the sterilization cap 50 is attached to the check valve unit 20 and the sterilization cap 50 is rotated.

Therefore, as another form of the groove shape of the cam groove 26*d*, two modifications shown in FIG. 14 and FIG. 15 are explained below. FIG. 14 and FIG. 15 respectively show two different modifications concerning the cam groove formed in the receiving ring of the check valve unit applied to the endoscope in the present embodiment and are development views of respective cam grooves.

A cam groove 26Ad in a first modification shown in FIG. 14 is an example in which a region including a vertex section is formed in a gentle R shape. A cam groove 26Bd in a second modification shown in FIG. 15 is an example configured such that a horizontal region D1 of a region including a vertex section is long compared with the same region D of the cam groove 26*d* in the first embodiment (see FIG. 13), that is, length of the region D1>length of the region D holds.

Both of ideas of groove shapes of the cam grooves (26Ad and 26Bd) in the respective modifications shown in FIG. 14 and FIG. 15 are ideas for controlling a period in which the communication path [AR] in the portion other than the valve structure of the check valve unit 20 is brought into the opening state and are configuration in which the open state of the communication path [AR] in a longer period can be maintained compared with the groove shape (see FIG. 13) of the cam groove 26*d* in the first embodiment.

Further, as a form of the cam groove shape, besides the two modifications explained above, for example, the cam groove shape may be configured to be a substantially perfect reverse V-shape as opposed to the substantial reverse V-shape shown in FIG. 13.

On the other hand, it is possible to change the movement amount H in the up-down direction of the receiving ring 26 by, for example, changing setting of length of the cam groove of the receiving ring 26 or the length L of the guide section 52*c* of the sterilization cap 50 substantially proportional to the length or changing the rotatable angle of the sterilization cap 50. Therefore, according to the respective setting changes, it is possible to make it easy to control an opening/closing state of the communication path [AR].

Figure 25:
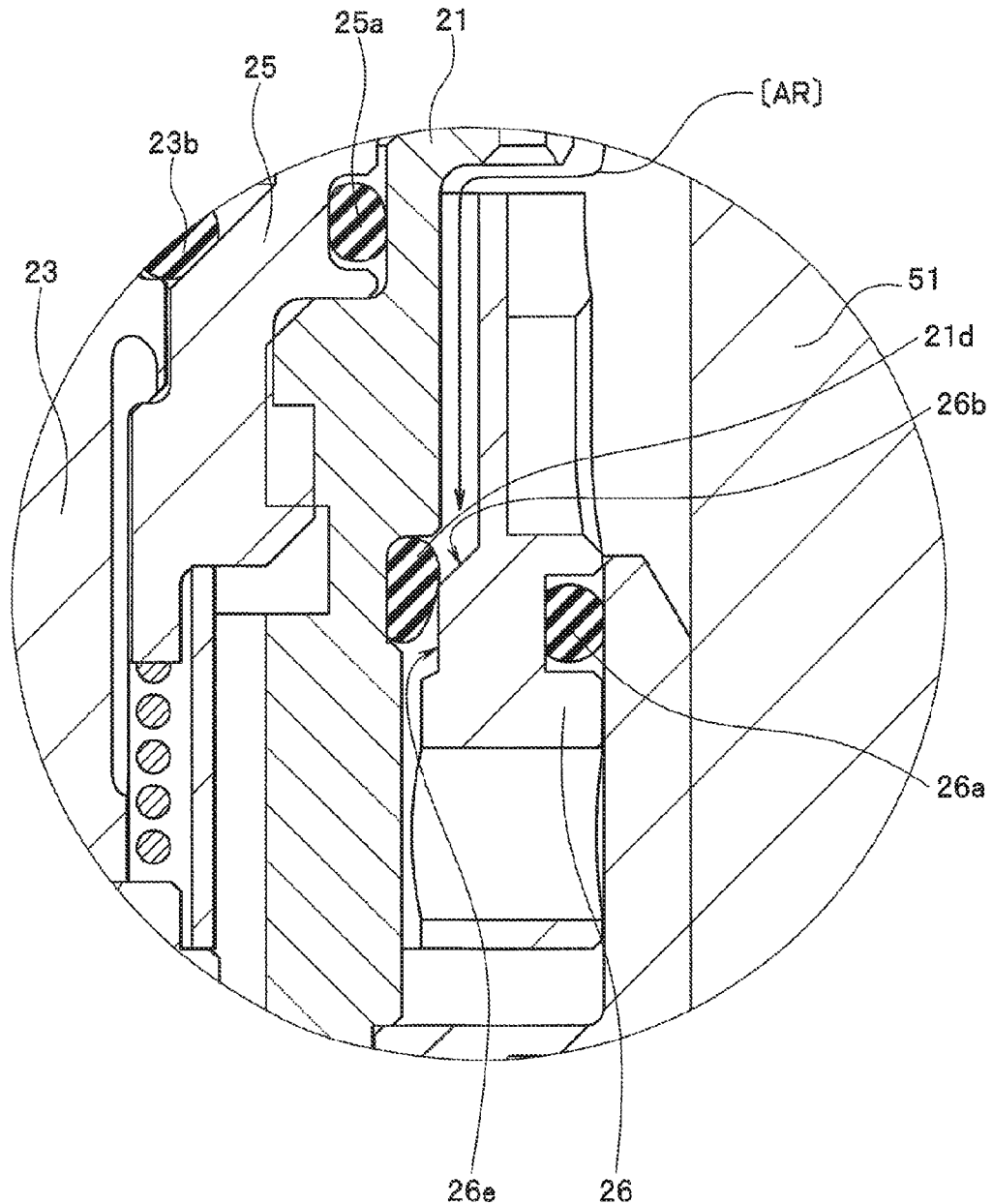
FIG. 25 is a main part enlarged sectional view showing another modification concerning a communication path [AR] in the check valve unit in the endoscope in the first embodiment of the present invention.

On the other hand, FIG. 25 is a main part enlarged sectional view showing another modification concerning the communication path [AR] in the check valve unit 20 in the first embodiment. Note that FIG. 25 shows a halfway progress at the time when the communication path [AR] gradually shifts from the closed state to the open state. That is, FIG. 25 shows a state in which a press-contact state of the O-shaped ring 21*d* and the taper surface 26*b* is not complete.

An example shown in FIG. 25 is an example in which a shape of a part on the receiving ring 26 side, with which the O-shaped ring 21*d* is in press-contact, that is, a vicinity of a contact part on an inner circumferential surface side of the receiving ring 26 is formed in a different shape. As shown in FIG. 25, the taper surface 26*b* is formed in the part. In this modification, a ventilation groove 26*e* having a form obtained by cutting out a part on the inner circumferential surface side of the receiving ring 26 from an intermediate part of the taper surface 26b is formed. By further providing such a ventilation groove 26e, the communication path [AR] can be configured to immediately change to the open state when a rotating operation of the sterilization cap 50 is started. Therefore, this is a configuration more effective when the open state is desired to be secured longer.

As explained above, according to the first embodiment, the communication path [AR] provided in the portion other than the valve structure of the check valve unit 20 is configured to be capable of being temporarily brought into the open state in the process for detaching the sterilization cap 50 after the end of various kinds of sterilization treatment, for example, the autoclave sterilization treatment. Therefore, with this configuration, the user can release the negative pressure state in the internal space of the endoscope 1 and surely set air pressure in the internal space to pressure substantially the same as the atmospheric pressure in the external space only by performing a procedure normally executed after the sterilization treatment, that is, a procedure for detaching the sterilization cap 50.

In that case, valve structures in the check valve unit 20 and the other ventilation valve units are not forcibly driven. Communication paths are provided in parts other than the valve structures. Therefore, it is possible to extremely easily perform communication of the internal space and the external space of the endoscope without spoiling original functions of the units including the valve structures and without causing deterioration of the units.

The ventilation valve unit provided separately from the check valve unit in the conventional endoscope can be made unnecessary.

Second Embodiment

A second embodiment of the present invention is explained below with reference to FIG. 26 to FIG. 36. A basic configuration in the present embodiment is substantially the same as that in the first embodiment explained above except that only a part of an internal configuration of a check valve unit applied to an endoscope is different. Therefore, components same as the components in the first embodiment are explained using the same reference numerals and signs. Detailed explanation of the same components is omitted. Only different parts are explained in detail below.

Figure 26:
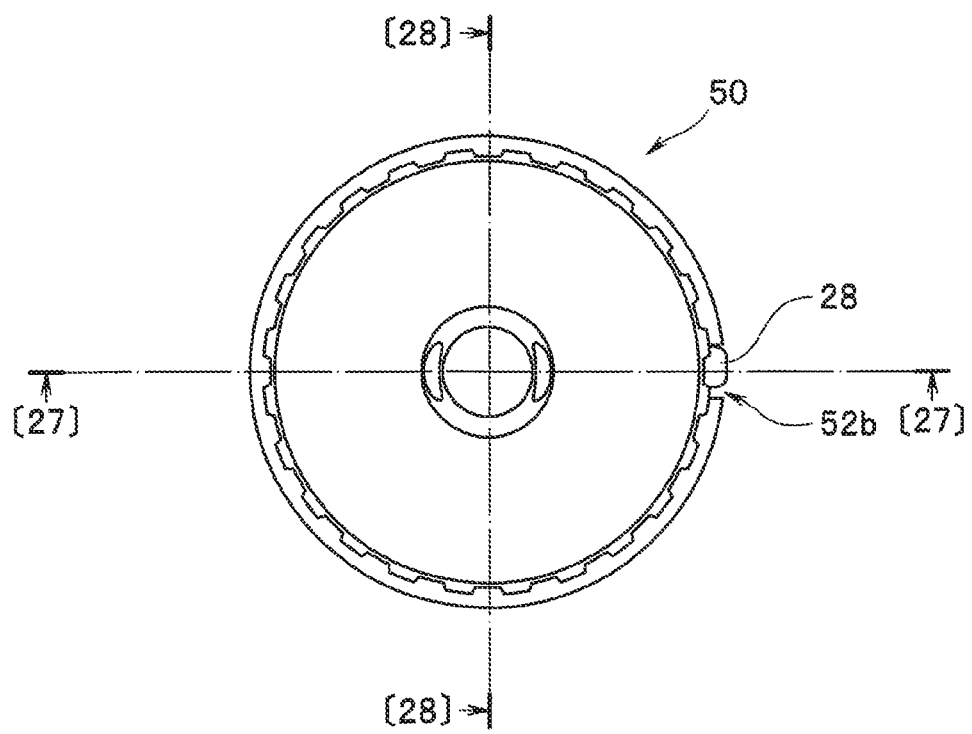
FIG. 26 is a top view during a closed state of a communication path in a state in which a sterilization cap is attached to a check valve unit in an endoscope in a second embodiment of the present invention.
Figure 27:
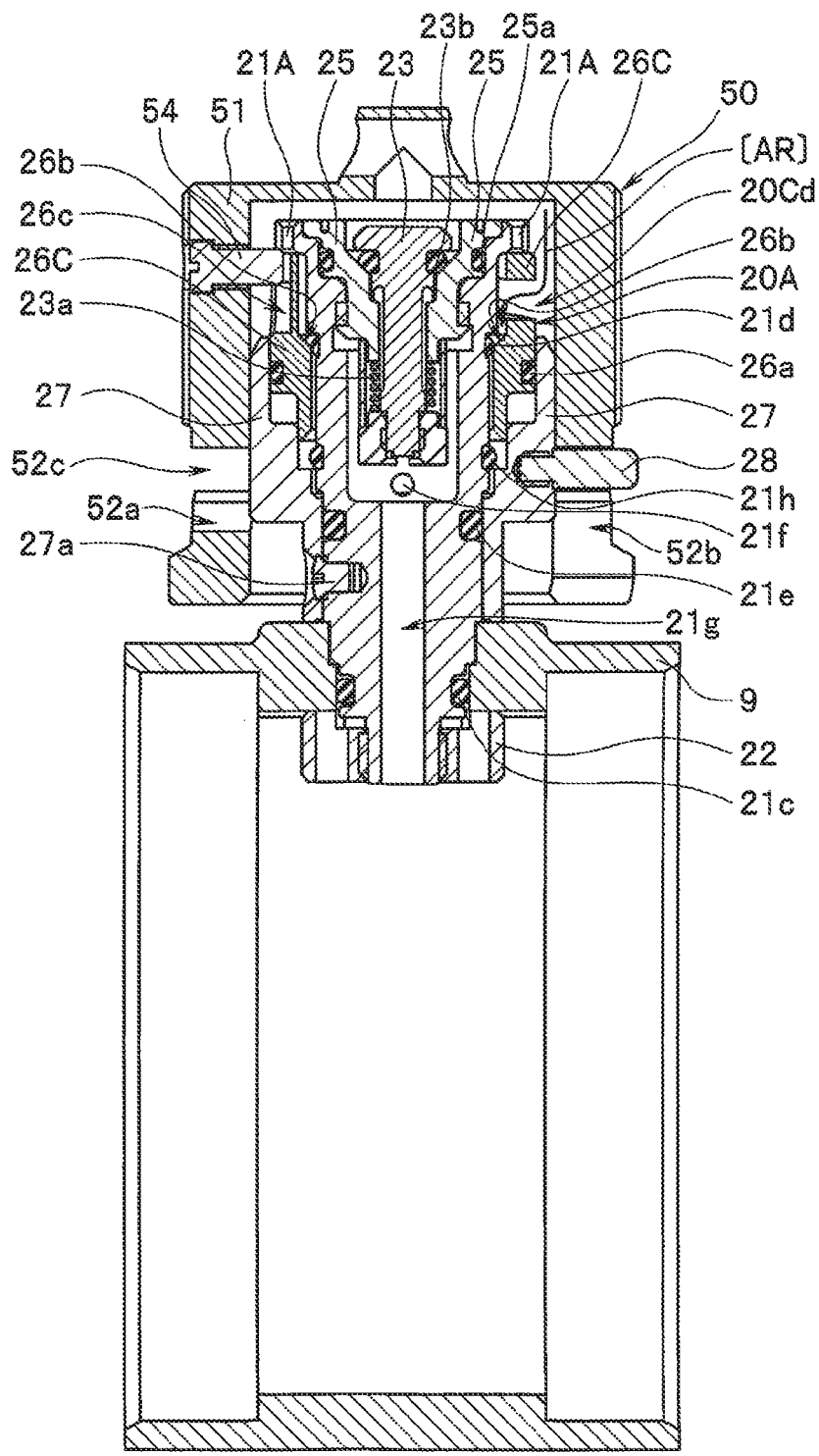
FIG. 27 is a sectional view taken along line [27]-[27] in FIG. 26.
Figure 28:
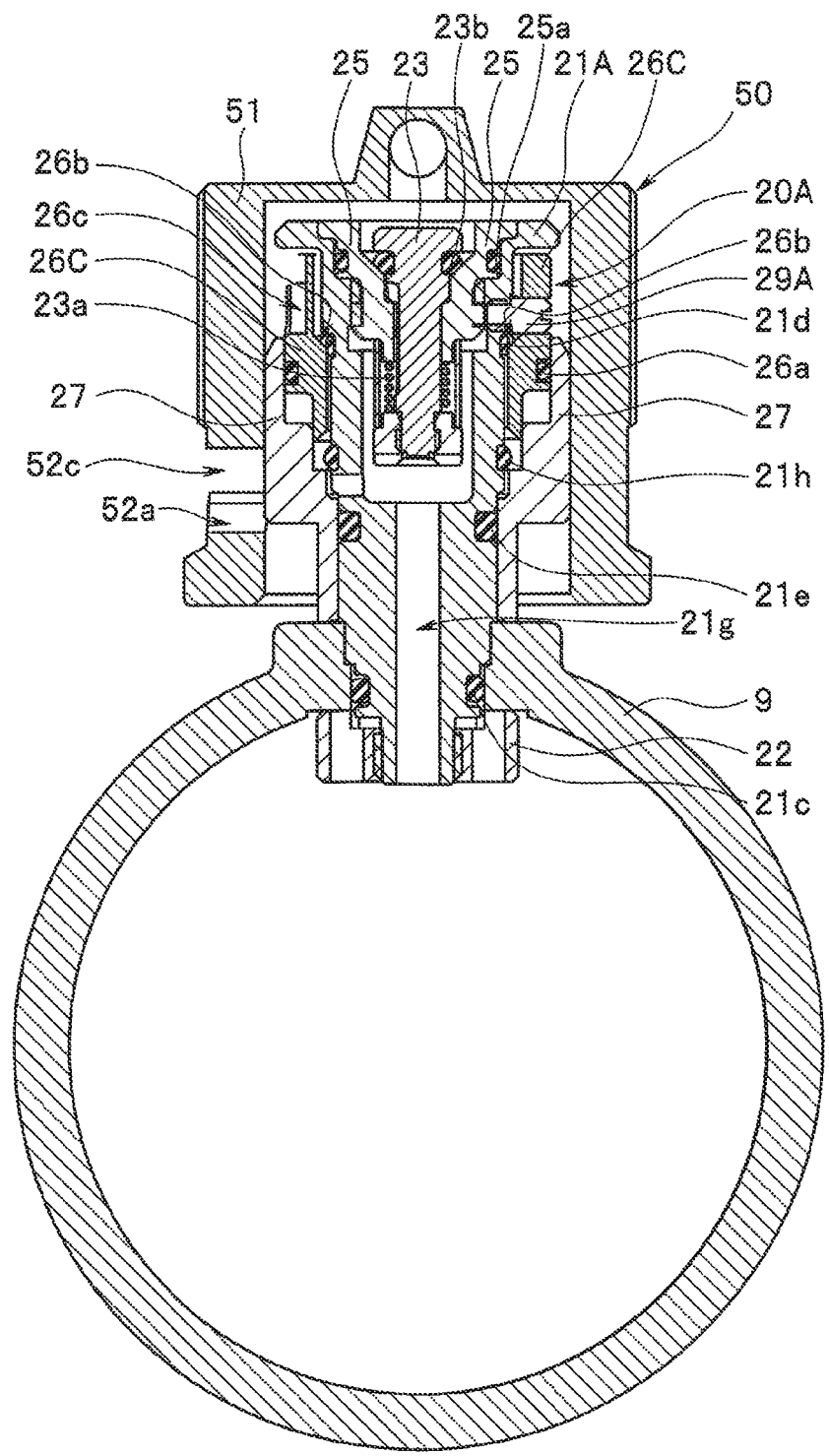
FIG. 28 is a sectional view taken along line [28]-[28] in FIG. 26.

FIG. 26 to FIG. 28 are diagrams showing a state in which a sterilization cap is attached to a check valve unit in an endoscope in the present embodiment. FIG. 26 to FIG. 28 correspond to FIG. 8 to FIG. 10 in the first embodiment. That is, FIG. 26 is a top view (during a closed state of a communication path). FIG. 27 is a side sectional view (a sectional view taken along line [27]-[27] in FIG. 26) viewed from a direction orthogonal to a long axis of a light guide connector. FIG. 28 is a side sectional view (a sectional view taken along line [28]-[28] in FIG. 26) viewed from a direction along the long axis of the light guide connector.

Figure 29:
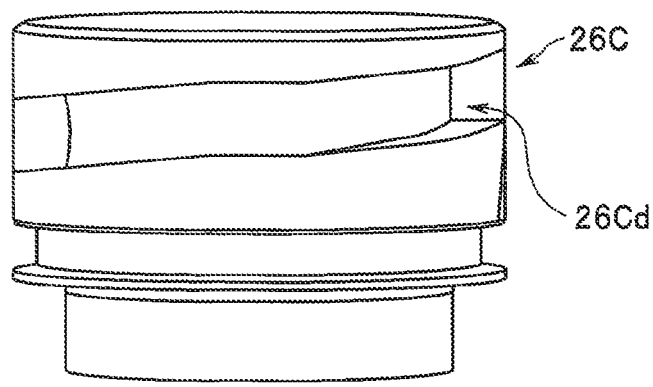
FIG. 29 is an exterior perspective view extracting and showing only a receiving ring among constituent members of a check valve unit in the endoscope in the second embodiment of the present invention.
Figure 30:
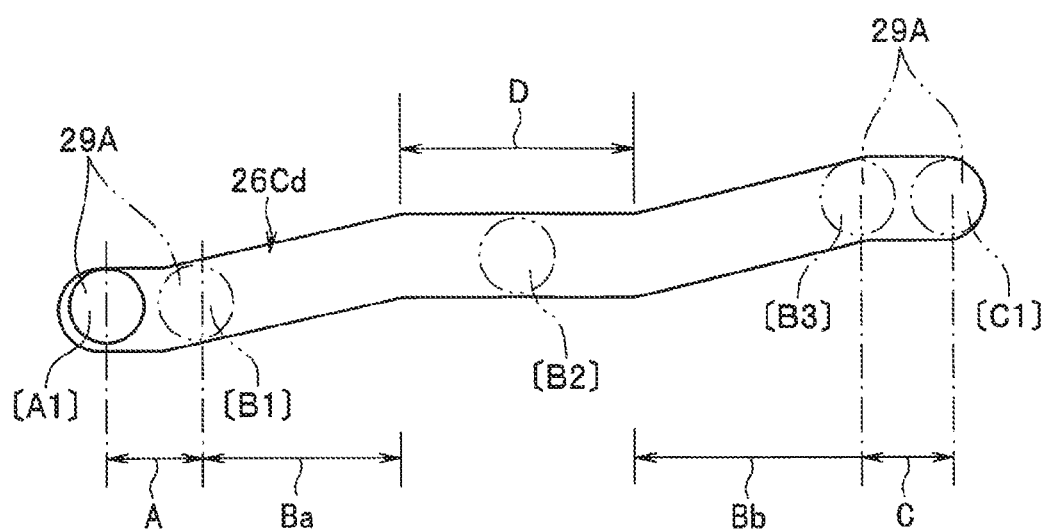
FIG. 30 is a development view enlarging and showing a cam shape of a cam groove formed in the receiving ring shown in FIG. 29.

FIG. 29 is an exterior perspective view extracting and showing only a receiving ring among constituent members of the check valve unit (corresponding to FIG. 11 in the first embodiment). FIG. 30 is a development view enlarging and showing a cam shape of a cam groove formed in the receiving ring shown in FIG. 29.

Figure 31:
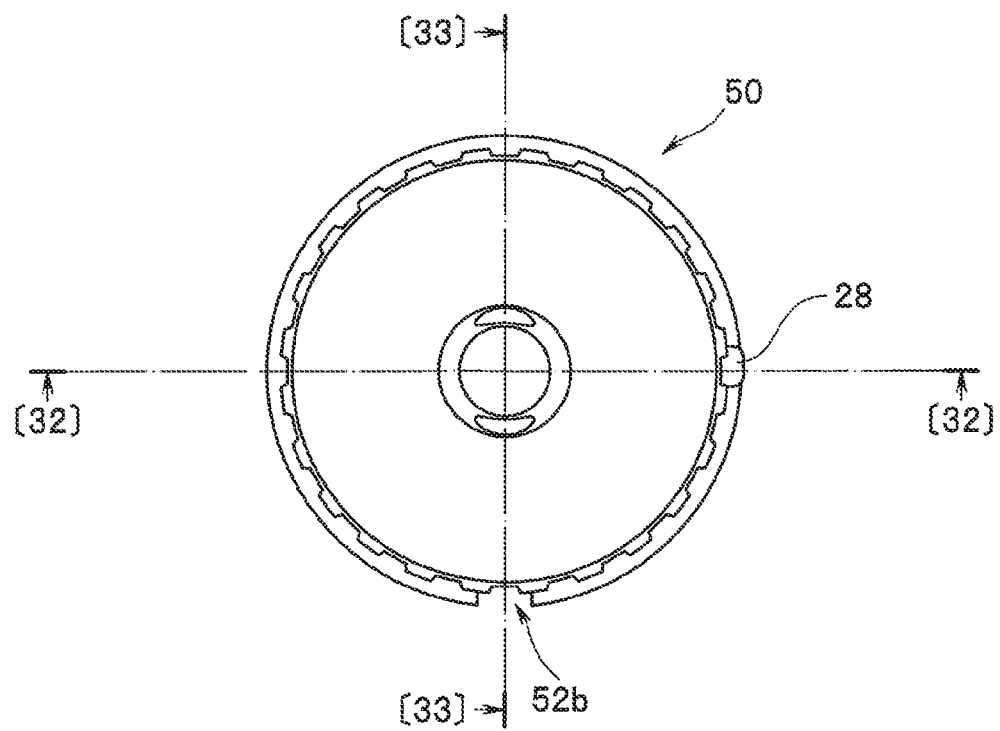
FIG. 31 is a top view showing action at the time when a sterilization cap is rotated by a predetermined rotation amount (θ=90 degrees) from the state shown in FIG. 26.
Figure 32:
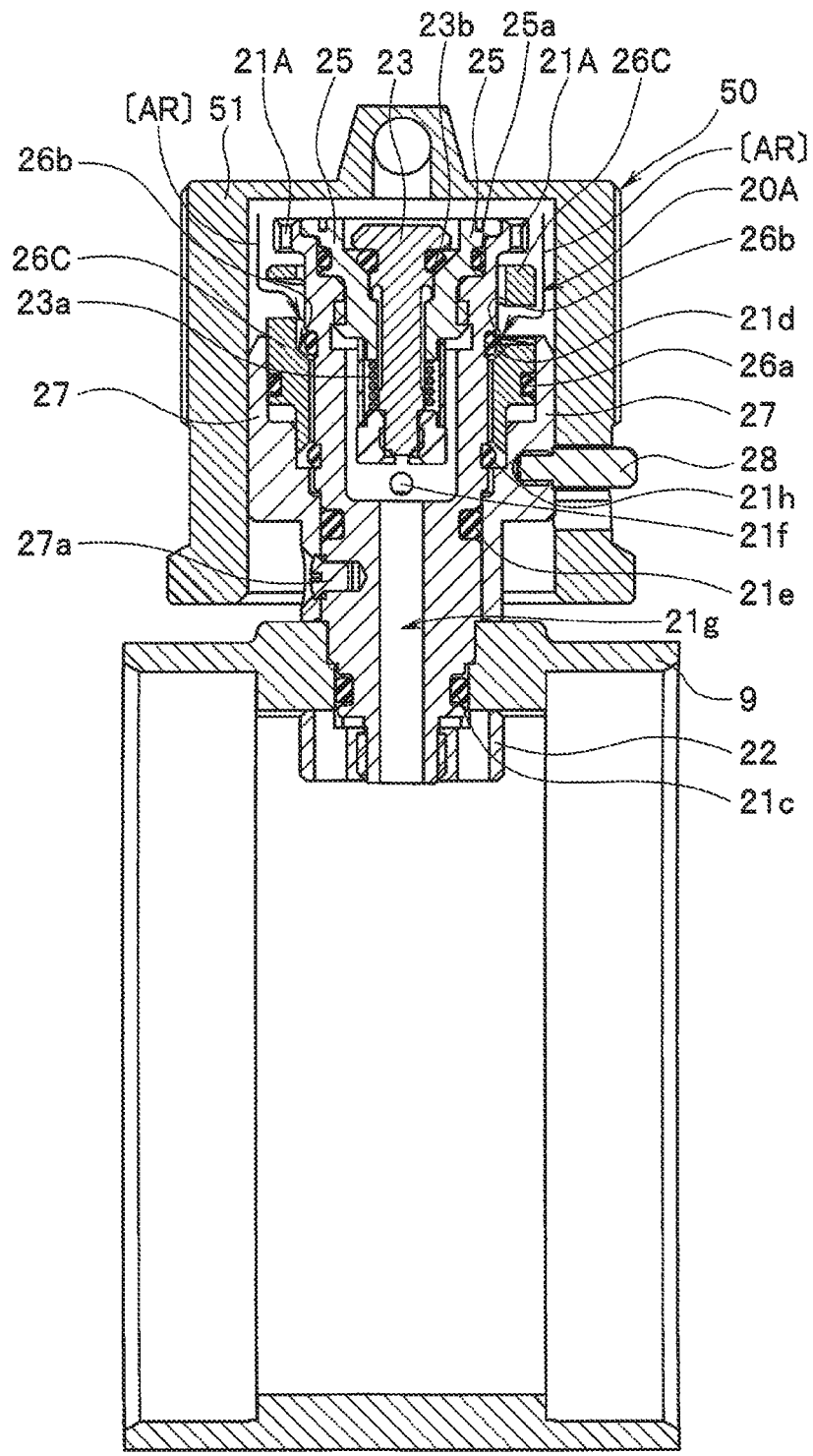
FIG. 32 is a sectional view taken along line [32]-[32] in FIG. 31.
Figure 33:
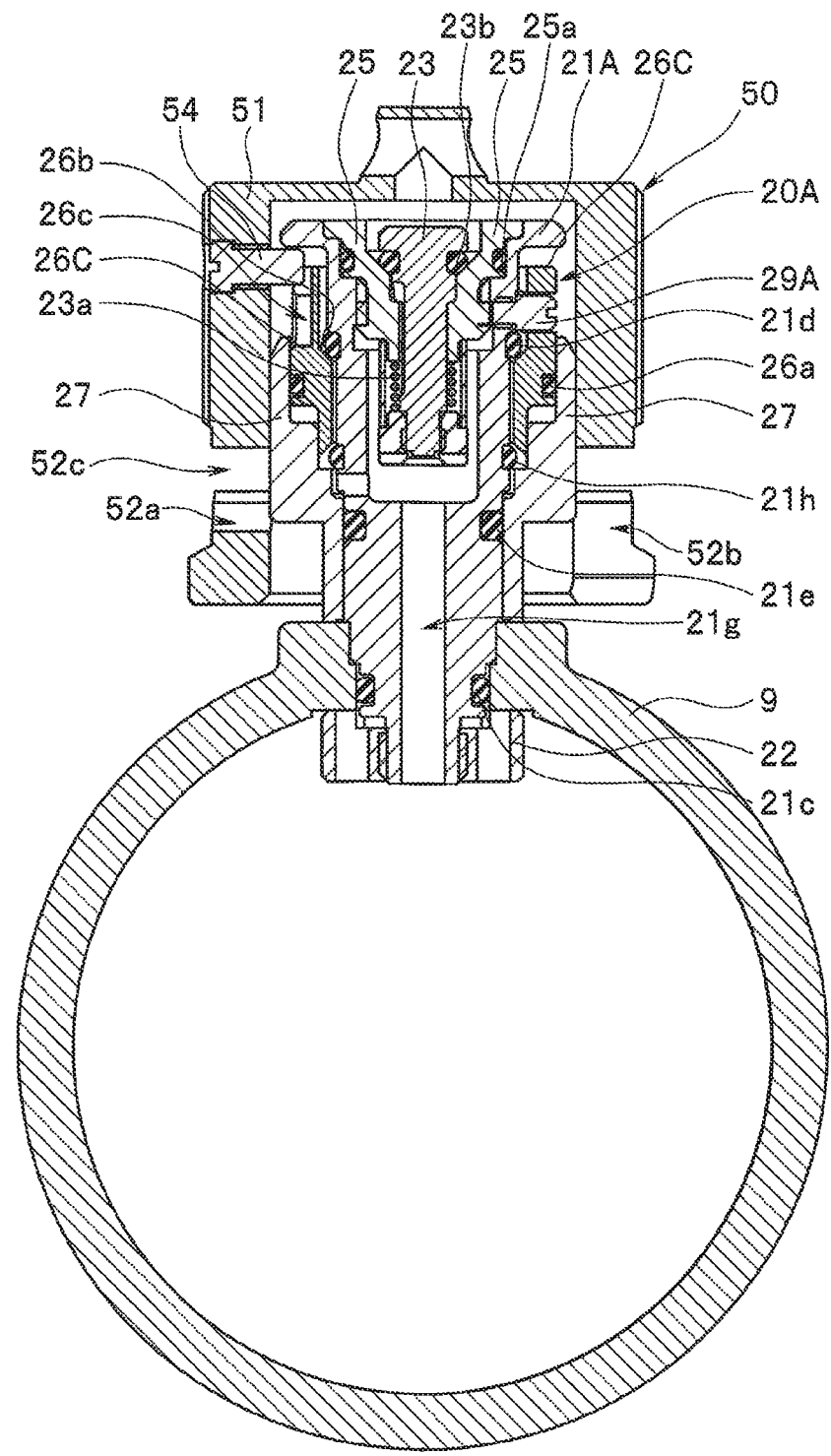
FIG. 33 is a sectional view taken along line [33]-[33] in FIG. 31.

FIG. 31 to FIG. 33 are diagrams showing a state in which a sterilization cap is rotated by a predetermined rotation amount (θ=90 degrees) from the state shown in FIG. 26 to FIG. 28 to bring a communication path [AR] of the check valve unit into an open state. Among the figures, FIG. 31 is a top view (during the open state of the communication path). FIG. 32 is a side sectional view (a sectional view taken along line [32]-[32] in FIG. 31) viewed from the direction orthogonal to the long axis of the light guide connector. FIG. 33 is a side sectional view (a sectional view taken along line [33]-[33] in FIG. 31) viewed from the direction along the long axis of the light guide connector.

Figure 34:
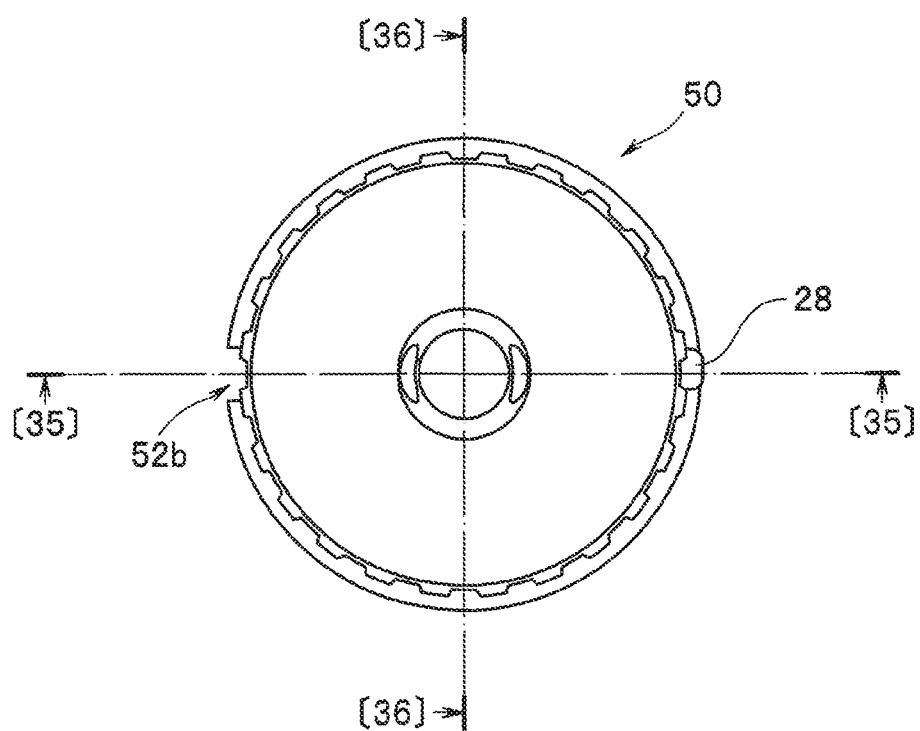
FIG. 34 is a top view showing action at the time when the sterilization cap is rotated by a predetermined rotation amount (θ=180 degrees) from the state shown in FIG. 26 and the sterilization cap is completely attached.
Figure 35:
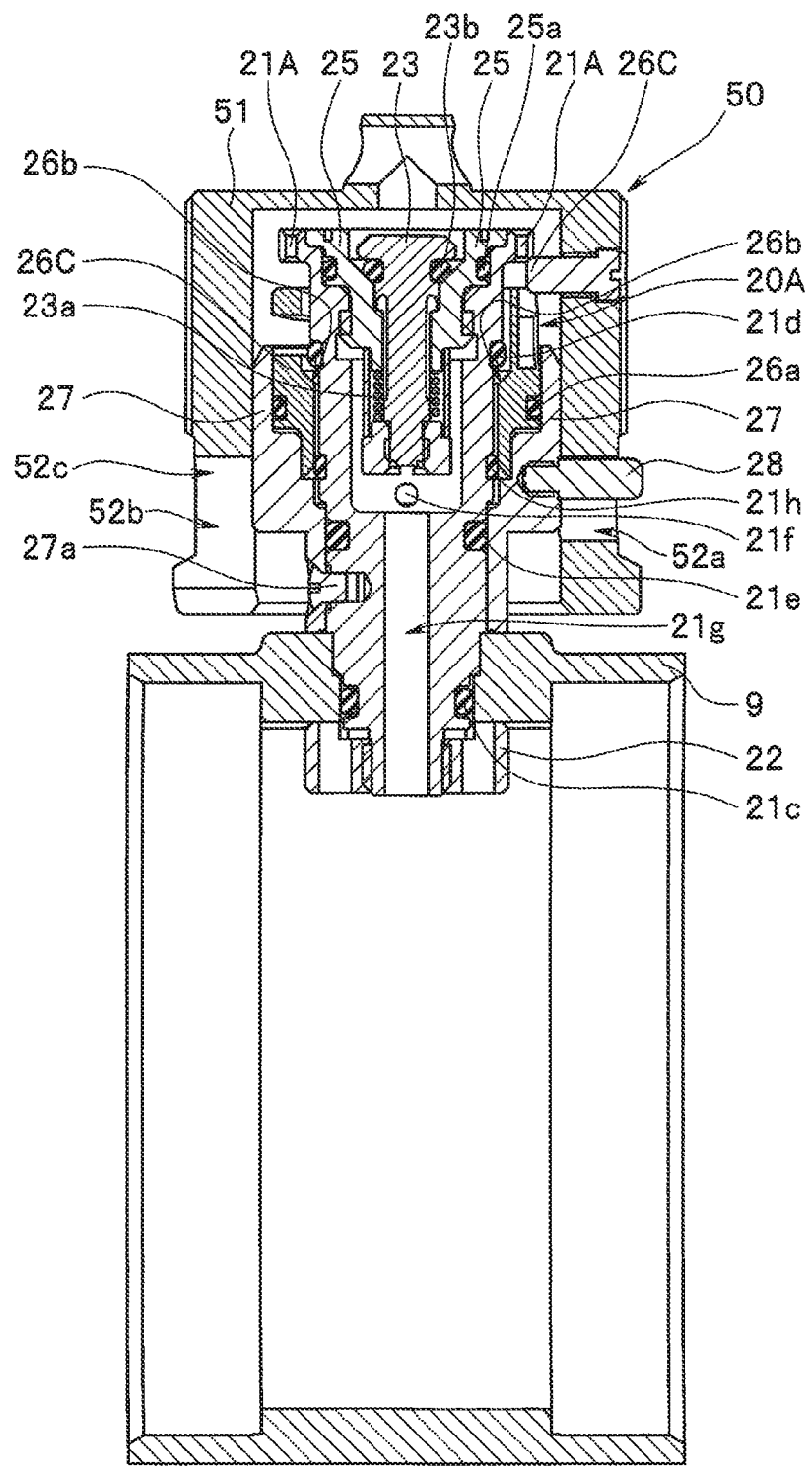
FIG. 35 is a sectional view taken along line [35]-[35] in FIG. 34.
Figure 36:
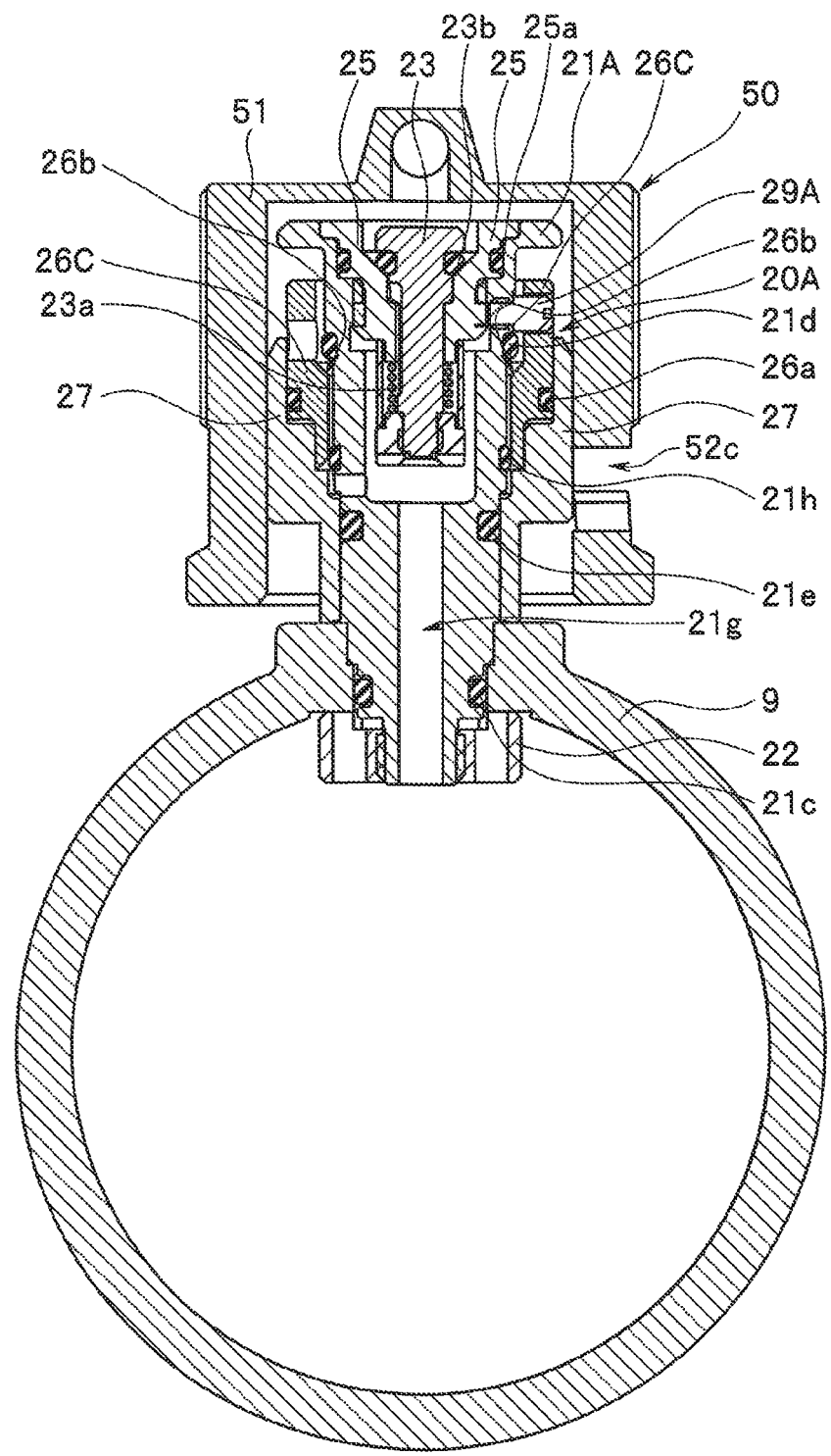
FIG. 36 is a sectional view taken along line [36]-[36] in FIG. 34.

FIG. 34 to FIG. 36 are diagrams showing a state in which the sterilization cap is rotated by a predetermined rotation amount (θ=180 degrees) from the state shown in FIG. 26 to FIG. 28 to completely attach the sterilization cap. Note that, at this point, the communication path [AR] of the check valve unit is in the closed state again. Among the figures, FIG. 34 is a top view (during the closed state of the communication path). FIG. 35 is a side sectional view (a sectional view taken along line [35]-[35] in FIG. 34) viewed from the direction orthogonal to the long axis of the light guide connector. FIG. 36 is a side sectional view (a sectional view taken along line [36]-[36] in FIG. 34) viewed from the direction along the long axis of the light guide connector.

The sterilization cap 50 in the endoscope in the present embodiment has a configuration completely the same as the configuration in the first embodiment.

A check valve unit 20A in the endoscope in the present embodiment is substantially the same as the check valve unit in the first embodiment and configured by constituent members such as a pipe sleeve main body section 21A, a receiving ring 26C, the reinforcing member 27, and the guide pin 28. Among the constituent members, configurations of the pipe sleeve main body section 21A and the receiving ring 26C are slightly different from the configurations in the first embodiment.

That is, the pipe sleeve main body section 21A in the present embodiment is different in that the pipe sleeve main body section 21A is configured to include two O-shaped rings 21d and 21h between the pipe sleeve main body section 21A and the receiving ring 26C in order to secure air tightness and water tightness between the pipe sleeve main body section 21A and the receiving ring 26C. The two O-shaped rings 21d and 21h are opening/closing sections that open and close the communication path [AR] at appropriate timing. The present embodiment is different from the first embodiment in that the opening/closing sections are provided in two places.

One O-shaped ring 21d of the two O-shaped rings 21d and 21h is provided in a part close to an upper end in an outer circumference side intermediate portion of the pipe sleeve main body section 21. When the check valve unit 20A is in a normal state, as shown in FIG. 27 and FIG. 28, the O-shaped ring 21d is in contact with the taper surface 26b formed in an inner circumference side intermediate portion of the receiving ring 26C. The O-shaped ring 21d is completely the same as the O-shaped ring 21d in the first embodiment.

Note that "when the check valve unit 20A is in the normal state" means a state in which the sterilization cap 50 is not attached to the check valve unit 20A or a state before the sterilization cap 50 is rotated after the sterilization cap 50 is attached to the check valve unit 20A (the state shown in FIG. 26 to FIG. 28). At this point, the communication path [AR] in the check valve unit 20A is in the closed state (see FIG. 27 and FIG. 28).

The other O-shaped ring 21h of the two O-shaped rings 21d and 21h is disposed in a part closer to a bottom than the O-shaped ring 21d in the outer circumference side intermediate portion of the pipe sleeve main body section 21 and disposed in a vicinity of an inner circumference side lower end edge portion of the receiving ring 26C. When the check valve unit 20A is in the normal state, the O-shaped ring 21h is in a state in which the O-shaped ring 21h is not in contact with an inner circumferential wall surface of the receiving ring 26C (see FIG. 27 and FIG. 28).

The two O-shaped rings 21d and 21h are attached to the outer circumference of the pipe sleeve main body section 21. In the normal state, the one O-shaped ring 21d comes into press-contact with the taper surface 26b of the receiving ring 26C to thereby seal a space between the pipe sleeve main body section 21 and the receiving ring 26C and bring the communication path [AR] into the closed state (see FIG. 27 and FIG. 28). As explained in detail below, when the receiving ring 26C moves a predetermined amount in a long axis direction of the check valve unit 20A from this normal state, the communication path [AR] is brought into the open state (see FIG. 32 and FIG. 33). When the receiving ring 26C further moves a predetermined amount in the same direction from this state, since the other O-shaped ring 21h comes into press-contact with the inner circumferential wall surface of the receiving ring 26C to thereby seal the space between the pipe sleeve main body section 21 and the receiving ring 26C again and brings the communication path [AR] into the closed state (see FIG. 35 and FIG. 36).

On the other hand, the receiving ring 26C in the present embodiment is formed as shown in FIG. 29. That is, the receiving ring 26C is opened at both ends and formed in a cylindrical shape as a whole. The receiving ring 26C is disposed to be rotatable around a long axis with respect to the pipe sleeve main body section 21A in a position where the receiving ring 26C covers an outer surface close to an upper end of the pipe sleeve main body section 21A. The receiving ring 26C is the same as the receiving ring in the first embodiment in that the receiving ring 26C is an opening/closing member that cooperates with the sterilization cap 50 and opens and closes the communication path [AR] in a portion other than a valve structure of the check valve unit 20A.

The receiving ring 26C is formed to include a fitting groove 26c and a cam groove 26Cd. The fitting groove 26c is a bottomed groove that engages with the cam operation pin 54 of the sterilization cap 50 when the sterilization cap 50 is attached to the check valve unit 20A. The fitting groove 26c is formed in a part and in a form same as the part and the form in the first embodiment. Action of the fitting groove 26c is also the same (not shown in FIG. 29. See FIG. 27 and the like).

The cam groove 26Cd is a cam groove to which the cam pin 29A of the pipe sleeve main body section 21A is coupled. The cam groove 26Cd is formed in a groove shape different from the groove shape of the cam groove 26d in the first embodiment. A disposed part of the cam groove 26Cd is different from the disposed part of the cam groove 26d in the first embodiment. That is, as shown in FIG. 29 and FIG. 30, the cam groove 26Cd of the receiving ring 26C in the present embodiment is formed as a through-groove extending in the circumferential direction along an outer circumferential surface close to an upper end of the receiving ring 26C.

Accordingly, as shown in FIG. 28, the cam pin 29A coupled to the cam groove 26Cd is provided projecting outward in a radial direction (a direction orthogonal to the long axis) of the pipe sleeve main body section 21A from an outer circumferential surface of the pipe sleeve main body section 21A in a part close to an upper end in a long axis direction of the pipe sleeve main body section 21A.

In the present embodiment, the cam groove shape of the cam groove 26Cd is formed, for example, as shown in FIG. 30. That is, the cam groove 26Cd is formed to include, in both end portions (a start point portion and an end point portion) and a substantially center portion (an intermediate portion) of the cam groove 26Cd, regions (regions indicated by signs A, Ba, D, Bb, and C in FIG. 30) parallel to a horizontal direction (a circumferential direction of the receiving ring 26C) and having predetermined lengths. The Ba region connecting the region A and the region D and the region Bb connecting the region D and the region C are respectively formed as upward inclined grooves. Note that, in the cam groove 26Cd in the present embodiment, the region A is set as a start point portion, the region Ba+the region D+the region Bb are set as an intermediate portion, and the region C is set as an end point portion.

As shown in FIG. 30 as well, the cam groove 26Cd in the present embodiment is formed in a direction along a rotating direction of the receiving ring 26C to continue from the region A (the start point portion) to the region C (the end point portion) stepwise.

In a process for attaching and detaching the sterilization cap 50 to and from the check valve unit 20A including the receiving ring 26C including the cam groove 26Cd configured in this way, when the receiving ring 26C rotates according to the rotation of the sterilization cap 50, the receiving ring 26C brings the communication path [AR] of the check valve unit 20A into the closed state when the cam pin 29A is present in the region A. At this point, the O-shaped ring 21d acts between the pipe sleeve main body section 21A and the receiving ring 26C to secure a sealed state.

Subsequently, while the cam pin 29A is shifting in the region Ba, the receiving ring 26C gradually brings the communication path [AR] into the open state according to action of the cam pin 29A and the cam groove 26Cd. When the cam pin 29A reaches the region D, the open state of the communication path [AR] by the receiving ring 26C is maximized. Note that the maximum open state is maintained while the cam pin 29A is shifting in the region D.

Subsequently, while the cam pin 29A is shifting in the region Bb, the receiving ring 26C gradually brings the communication path [AR] into the closed state according to action of the cam pin 29A and the cam groove 26Cd. When the cam pin 29A shifts to the region C, the receiving ring 26C brings the communication path [AR] of the check valve unit 20A into the closed state. At this point, the O-shaped ring 21h acts between the pipe sleeve main body section 21A and the receiving ring 26C to secure a sealed state.

Note that, in the present embodiment, a disposed position of the cam operation pin 54 fit in the fitting groove 26c of the receiving ring 26C (see FIG. 27) and a disposed position of the cam pin 29A coupled to the cam groove 26Cd of the receiving ring 26C (see FIG. 28) are disposed in positions shifted by an angle of approximately 90 degrees in the rotating direction, for example, when viewed from an upper surface side. The other components are substantially the same as the components in the first embodiment.

Action in attaching and detaching the sterilization cap 50 to and from the check valve unit 20A in the endoscope in the present embodiment is explained in detail below with reference to FIG. 26 to FIG. 28, FIG. 30, and FIG. 31 to FIG. 36.

A procedure in attaching the sterilization cap 50 to the check valve unit 20A is the same as the procedure in the first embodiment. That is, first, the user aligns the lead-in section 52b of the guide groove 52 of the sterilization cap 50 and the guide pin 28 of the check valve unit 20A, engages the guide pin 28 along the lead-in section 52b, and fits the cam operation pin 54 of the sterilization cap 50 in the fitting groove 26c of the receiving ring 26C. When the sterilization cap 50 is rotated in a predetermined direction in this state, the receiving ring 26C rotates in the same direction.

In a state before the sterilization cap 50 is attached to the check valve unit 20A, the cam pin 29A is present in the cam groove 26Cd and present in, for example, a position indicated by [A1] in FIG. 30. At this point, as shown in FIG. 27 and FIG. 28, the check valve unit 20A secures a sealed state of the inside and the outside of the endoscope 1 with the valve structure. A sealed state is secured by the O-shaped ring 21d between the pipe sleeve main body section 21A and the receiving ring 26C. That is, at this point, the communication path [AR] is also in the closed state (see, in particular, FIG. 27).

When the cam pin 29A is present in the [A1] position in FIG. 30 in the cam groove 26Cd, when the user rotates the sterilization cap 50 in the predetermined direction and rotates the receiving ring 26C in the same direction, the cam pin 29A moves relatively to the sterilization cap 50 and reaches the [B1] position in FIG. 30. In a region reaching from [A1] to [B1] in FIG. 30, that is, the region A in the figure, the cam pin 29A only moves a predetermined distance in the horizontal direction (the circumferential direction) relatively to the sterilization cap 50. Therefore, in a period of the movement in region A, the cam pin 29A does not act on the cam groove 26Cd. The sealed state of the check valve unit 20A is maintained in this period.

Subsequently, similarly, when the sterilization cap 50 is rotated in the same direction and the receiving ring 26C rotates in the same direction, the cam pin 29A relatively moves from the [B1] position in FIG. 30 to the [B2] position in the figure in the cam groove 26Cd. The [B2] position in FIG. 30 is any position in the D region. The cam groove 26Cd is an inclined groove facing upward in a period from the [B1] position to the [B2] position in FIG. 30. Therefore, when the time when the cam pin 29A relatively moves along the upward inclined groove of the cam groove 26Cd, the receiving ring 26C moves downward along the long axis direction of the pipe sleeve main body section 21A. A state at this point is shown in FIG. 31 to FIG. 33.

In this state, as shown in FIG. 32, FIG. 33, and the like, a gap is formed between the pipe sleeve main body section 21A and the taper surface 26b of the receiving ring 26C by the O-shaped ring 21d. On the other hand, in this state, the O-shaped ring 21h is not in contact with the receiving ring 26C. Therefore, the communication path [AR] formed between the pipe sleeve main body section 21A and the receiving ring 26C is in the open state. Consequently, the internal space and the external space of the endoscope 1 communicate with each other via the communication path [AR].

Note that the region D of the cam groove 26Cd is formed in the horizontal direction (the circumferential direction) by a predetermined length. With this configuration, when the cam pin 29A is present in the region D, the maximum open state of the communication path [AR] is maintained.

Subsequently, similarly, when the sterilization cap 50 is rotated in the same direction and the receiving ring 26C rotates in the same direction, the cam pin 29A relatively moves from the [B2] position in FIG. 30 to the [B3] position in the figure in the cam groove 26Cd. In a period from the [B2] position to the [B3] position in FIG. 30 (the region Bb), the cam groove 26Cd is an inclined groove facing upward as in the region Ba. Therefore, when the cam pin 29A relatively moves along the upward inclined groove of the cam groove 26Cd, the receiving ring 26C moves downward along the long axis direction of the pipe sleeve main body section 21A. A state at this point is shown in FIG. 34 to FIG. 36.

In this state, as shown in FIG. 35, FIG. 36, and the like, the gap is still formed between the pipe sleeve main body section 21A and the taper surface 26b of the receiving ring 26C by the O-shaped ring 21d. However, on the other hand, the O-shaped ring 21h is in press-contact with the inner circumferential wall surface of the receiving ring 26C. Therefore, the communication path [AR] formed between the pipe sleeve main body section 21A and the receiving ring 26C changes to the closed state. Consequently, the internal space and the external space of the endoscope 1 are sealed again.

After the cam pin 29A reaches the [B3] position in FIG. 30 in the cam groove 26Cd and the communication path [AR] is brought into the closed state, when the user further rotates the sterilization cap 50 in the predetermined direction, the cam pin 29A reaches from the [B3] position to the [C1] position in FIG. 30. In a region reaching from [B3] to [C1], that is, the region C in FIG. 30, as in the region A in the figure, the cam pin 29A only moves a predetermined distance in the horizontal direction (the circumferential direction) relatively to the sterilization cap 50. Therefore, in a period of the movement in region C, the cam pin 29A does not act on the cam groove 26Cd. Consequently, the sealed state of the check valve unit 20A is maintained in the period.

In this way, the sterilization cap 50 is completely attached to the check valve unit 20A. At this point, the internal space and the external space of the endoscope 1 is in the sealed state by the check valve unit 20A. The communication path [AR] is in the closed state.

In this state, the endoscope 1 is placed in the autoclave sterilization treatment apparatus and autoclave sterilization treatment is applied to the endoscope 1. After the sterilization treatment ends, the internal space of the endoscope 1 is in a negative pressure state. When the endoscope 1 is taken out from the autoclave sterilization treatment apparatus and the sterilization cap 50 is detached from the check valve unit 20A, in a process for detaching the sterilization cap 50, the communication path [AR] temporarily changes to the open state. Consequently, the negative pressure state of the internal space of the endoscope 1 is released. The other action is substantially the same as the action in the first embodiment.

As explained above, according to the second embodiment, it is possible to obtain effects same as the effects of the first embodiment.

Note that, in the configuration of the present embodiment, compared with the configuration of the first embodiment, a moving stroke in the axial direction of the receiving ring is different and the disposed position of the cam groove of the receiving ring is different. In this case, the configuration of the first embodiment is a configuration advantageous for a reduction in size as a configuration in which the communication path is provided in the check valve unit. More specifically, since the moving stroke of the receiving ring is small, it is possible to reduce a projection amount of the check valve unit from the endoscope surface. Therefore, there is an advantage that convenience of use (usability) is high for the user. In the configuration of the first embodiment, there is also an advantage that the endoscope can be manufactured inexpensively because a mechanism can be further simplified. Therefore, when the present invention is carried out, the configuration of the first embodiment is a best mode.

Note that the present invention is not limited to the embodiments explained above. Various modifications and applications can be implemented within a range not departing from the spirit of the invention. Further, inventions in various stages are included in the embodiments. Various inventions can be extracted according to appropriate combinations in a disclosed plurality of constituent elements. For example, when the problems to be solved by the invention can be solved and the effects of the invention can be obtained even if several constituent elements are deleted from all the constituent elements described in the one embodiment, a configuration from which the constituent elements are deleted can be extracted as an invention.

INDUSTRIAL APPLICABILITY

The present invention can be applied not only to an endoscope control apparatus in a medical field but also to an endoscope control apparatus in an industrial field.

What is claimed is:

1. An endoscope comprising:
a partition wall configured to shield an inner side space and an outer side space;
a cylindrical body including an internal wall surface coupled to the partition wall to be capable of being water tight, the internal wall surface forming a communication hole communicating with the inner side space, and including a through-hole piercing through the internal wall surface to an outer circumference;
a valve body fixed to the communication hole while keeping water tightness and including a check valve section that performs opening and closing operations according to a pressure difference between the inner side space and the outer side space;
a first frame body provided on an outer circumference side of the cylindrical body and configured to be capable of operating in an axial direction of the cylindrical body;
a second frame body sheathed over the cylindrical body and the first frame body while keeping the water tightness, the second frame body forming a first space communicating with the through-hole; and
a water-tight member disposed between the cylindrical body and the first frame body, the water-tight member switching opening/closing states of the first space and the outer side space when the first frame body operates in the axial direction.

2. The endoscope according to claim 1, further comprising:
a cam pin provided on an outer circumferential surface of the cylindrical body; and
a cam groove provided in the first frame body, disposed to be capable of sliding with respect to the cam pin, guided by the cam pin, and including a start point portion, an intermediate portion, and an end point portion, wherein
the first frame body operates in the axial direction when the cam groove slides with respect to the cam pin.

3. The endoscope according to claim 2, wherein, in the cam groove, the intermediate portion is formed in a substantially reverse V-shape toward the axial direction.

4. The endoscope according to claim 3, wherein length in a circumferential direction of the intermediate section of the cam groove is formed larger than length of the start point portion or the end point portion.

5. The endoscope according to claim 4, wherein
when the cam pin is located in the start point portion or the end point portion, a space between the first space and the outer side space is shielded, and
when the cam pin is located in the intermediate portion, the space between the first space and the outer side space is opened.

6. The endoscope according to claim 5, further comprising:
a cap attachable to the second frame body; and
an operation pin provided in the cap, capable of being locked to the first frame body, and capable of rotating the first frame body around an axis of the cylindrical body.

7. The endoscope according to claim 6, further comprising:
a guide groove formed in a rotating direction of the cap;
a guide pin projectingly provided on the second frame body, received in the guide groove, and relatively disposed in a predetermined position in the guide groove according to the rotation of the cap.

8. The endoscope according to claim 7, wherein
the guide groove includes a base portion, an intermediate portion, and an end portion,
the cam pin is located in the start point portion or the end point portion of the cam groove when the guide pin is located in the base portion or the end portion, and
the cam pin is located in the intermediate portion of the cam groove when the guide pin is located in the intermediate portion.

9. The endoscope according to claim 8, wherein
when the cap is attached to the second frame body and the guide pin is located at the end portion of the guide groove, the space between the first space and the outer side space is shielded,
in a process in which the cap is detached from the second frame body,
the first frame body is rotated by the operation pin,
the cam pin is guided to the intermediate portion of the cam groove,
the first space is opened to the outer side space when the first frame body moves in the axial direction, and
when the cap is completely detached from the second frame body,
the first frame body moves in the axial direction and returns to an original position with the operation pin, the cam pin, and the cam groove, and the space between the first space and the outer side space is shielded.

10. The endoscope according to claim 2, wherein the cam groove is continuously formed along a rotating direction of the first frame body stepwise from the start point portion to the end point portion.

11. An endoscope comprising:
a partition wall configured to separate an inner side space from an outer side space;
a cylindrical body including an internal wall surface water-tightly coupled to the partition wall, the internal wall surface forming a communication hole communicating with the inner side space, the cylindrical body further having a through-hole piercing through the internal wall surface to an outer circumference of the internal wall surface;
a valve body fixed to the communication hole while keeping water tightness and including a check valve section that performs opening and closing operations through the communication hole according to a pressure difference between the inner side space and the outer side space;
a first frame body provided on an outer circumference side of the cylindrical body and configured to be movable in an axial direction relative to the cylindrical body;
a second frame body sheathed over the cylindrical body and the first frame body while keeping the water tightness, the second frame body forming a first space communicating with the through-hole; and
a water-tight member disposed between the cylindrical body and the first frame body, the water-tight member switching opening/closing states of the first space and the outer side space through the through-hole when the first frame body moves in the axial direction.

* * * * *